US00RE45666E

(19) United States
(12) Reissued Patent
Feldstein et al.

(10) Patent Number: US RE45,666 E
(45) Date of Reissued Patent: Sep. 8, 2015

(54) PREPARATION OF HYDROPHILIC PRESSURE SENSITIVE ADHESIVES HAVING OPTIMIZED ADHESIVE PROPERTIES

(71) Applicants: A.V. TOPCHIEV INSTITUTE OF PETROCHEMICAL SYNTHESIS, Moscow (RU); CORIUM INTERNATIONAL, INC., Menlo Park, CA (US); Olga N. Emanuel, Moscow (RU)

(72) Inventors: Mikhail M. Feldstein, Moscow (RU); Nicolai A. Platè, Moscow (RU); Anatoly E. Chalykh, Moscow (RU); Gary W. Cleary, Los Altos Hills, CA (US)

(73) Assignees: A.V. Topchiev Institute of Petrochemical Synthesis, Moscow (RU); Corium International, Inc., Menlo Park, CA (US)

(21) Appl. No.: 13/761,118

(22) Filed: Feb. 6, 2013

Related U.S. Patent Documents

Reissue of:

(64) Patent No.: 6,576,712
Issued: Jun. 10, 2003
Appl. No.: 09/900,697
Filed: Jul. 6, 2001

U.S. Applications:

(63) Continuation of application No. 11/150,811, filed on Jun. 10, 2005, now Pat. No. Re. 44,145, which is an application for the reissue of Pat. No. 6,576,712, which is a continuation-in-part of application No. 09/847,532, filed on May 1, 2001, now abandoned.

(60) Provisional application No. 60/216,386, filed on Jul. 7, 2000.

(51) Int. Cl.

| | |
|---|---|
| ***C08J 3/24*** | (2006.01) |
| ***C08F 26/00*** | (2006.01) |
| ***A61L 15/16*** | (2006.01) |
| ***A61K 9/70*** | (2006.01) |
| ***A61L 15/58*** | (2006.01) |

(52) U.S. Cl.
CPC ..... *A61L 15/58* (2013.01); *A61K 9/7053* (2013.01)

(58) Field of Classification Search
USPC ..... 525/326.9, 92 B, 384, 118; 524/386; 424/448
See application file for complete search history.

(56) References Cited

U.S. PATENT DOCUMENTS

| | | | |
|---|---|---|---|
| 2,561,071 | A | 7/1951 | Prisk |
| 2,579,403 | A | 12/1951 | Slomowitz et al. |
| 3,150,977 | A | 9/1964 | Hart et al. |
| 3,689,439 | A | 9/1972 | Field et al. |
| 3,721,657 | A | 3/1973 | Seiderman |
| 3,749,755 | A | 7/1973 | Bronstart et al. |
| 3,852,228 | A | 12/1974 | Brothers |
| 3,957,605 | A | 5/1976 | Assarsson et al. |
| 3,993,551 | A | 11/1976 | Assarsson et al. |
| 3,996,934 | A | 12/1976 | Zaffaroni |
| 4,091,090 | A | 5/1978 | Sipos |
| 4,093,673 | A | 6/1978 | Chang et al. |
| 4,160,020 | A | 7/1979 | Ayer et al. |
| 4,231,369 | A | 11/1980 | Sorensen et al. |
| 4,277,580 | A | 7/1981 | Allen et al. |
| 4,325,851 | A | 4/1982 | Colon et al. |
| 4,346,709 | A | 8/1982 | Schmitt et al. |
| 4,367,732 | A | 1/1983 | Poulsen et al. |
| 4,492,685 | A | 1/1985 | Keith et al. |
| 4,529,601 | A | 7/1985 | Broberg et al. |
| 4,552,751 | A | 11/1985 | Inaba et al. |
| 4,557,934 | A | 12/1985 | Cooper |
| 4,562,060 | A | 12/1985 | Broberg et al. |
| 4,568,343 | A | 2/1986 | Leeper et al. |
| 4,587,289 | A | 5/1986 | Comert et al. |
| 4,593,053 | A | 6/1986 | Jevne et al. |

(Continued)

FOREIGN PATENT DOCUMENTS

| | | |
|---|---|---|
| CA | 2520986 | 4/2000 |
| CA | 2402021 | 9/2001 |

(Continued)

OTHER PUBLICATIONS

U.S. Appl. No. 11/150,811, filed Jun. 10, 2005, Feldstein et al.
U.S. Appl. No. 12/687,586, filed Jan. 11, 2009, Singh et al.
"Aquasorb® A-500 Cellulose Gum (CMC)", Hercules Incorporated, Aqualon Division, Product Data No. 4234, 2 pgs. (2005).
Barbucci et al. "Swelling behavior of carboxymethylcellulose hydrogels in relation to cross-linking, pH, and charge density", Macromolecules, vol. 33, No. 20, pp. 7475-7480 (2000).
Feldstein et al., "A new class of pressure-sensitive adhesives based on interpolyrrier and polymer-oligomer complexes", Polymer Science, vol. 51, No. 7, pp. 799-814 (2009).
International Search Report for PCT/US2005/0034439 Mailed Jul. 19, 2006.
International Search Report for PCT/US2005/0046577 Mailed Jul. 26, 2006.
International Search Report for PCT/US/2005/028063 Mailed Apr. 28, 2006.
International Search Report for PCT/US/2005/032525 Mailed Mar. 17, 2006.

(Continued)

*Primary Examiner* — Irina S Zemel
(74) *Attorney, Agent, or Firm* — Susan T. Evans; McDermott Will & Emery LLP

(57) ABSTRACT

A method for preparing hydrophilic pressure sensitive adhesive (PSA) compositions is provided, wherein the method enables preparation of adhesives having a particular, optimized degree of adhesion. That is, the hydrophilic PSA is comprised of a hydrophilic polymer and a complementary short-chain plasticizing agent, wherein the hydrophilic polymer and plasticizing agent are capable of hydrogen bonding or electrostatic bonding to each other and are present in a ratio that optimizes key characteristics of the adhesive composition, such as adhesive strength, cohesive strength and hydrophilicity. The adhesive is useful in a wide variety of contexts, e.g., as a biomedical adhesive for application to the skin or other body surface, and as such finds utility in the areas of drug delivery systems (e.g., topical, transdermal, transmucosal, iontophoretic), medical skin coverings and wound healing products and biomedical electrodes.

64 Claims, 6 Drawing Sheets

(56) References Cited

U.S. PATENT DOCUMENTS 4,624,665 A 11/1986 Nuwayser
4,699,146 A 10/1987 Sieverding
4,713,243 A 12/1987 Schiraldi et al.
4,743,249 A 5/1988 Loveland
4,750,482 A 6/1988 Sieverding
4,771,105 A 9/1988 Shirai et al.
4,849,224 A 7/1989 Chang et al.
4,863,738 A 9/1989 Taskovich
4,863,970 A 9/1989 Patel et al.
4,867,748 A 9/1989 Samuelsen
4,871,536 A 10/1989 Arraudeau et al.
4,873,299 A 10/1989 Nowakowsky et al.
4,877,628 A 10/1989 Stypula
4,904,247 A 2/1990 Therriault et al.
4,906,169 A 3/1990 Chien et al.
4,927,408 A 5/1990 Haak et al.
4,945,084 A 7/1990 Packman
4,953,053 A 8/1990 Pratt
4,973,468 A 11/1990 Chiang et al.
4,983,395 A 1/1991 Chang et al.
5,023,084 A 6/1991 Chien et al.
5,053,227 A 10/1991 Chiang et al.
5,057,500 A 10/1991 Thornfeldt
5,073,381 A 12/1991 Ivan et al.
5,102,662 A 4/1992 Gallagher
5,125,894 A 6/1992 Phipps et al.
5,133,970 A 7/1992 Petereit et al.
5,141,750 A 8/1992 Lee et al.
5,173,302 A 12/1992 Holmblad et al.
5,183,901 A 2/1993 Login et al.
5,196,405 A 3/1993 Packman
5,200,190 A 4/1993 Azuma et al.
5,206,385 A 4/1993 Login et al.
5,224,928 A 7/1993 Sibalis et al.
5,232,702 A 8/1993 Pfister et al.
5,234,690 A 8/1993 Chiang et al.
5,234,957 A 8/1993 Mantelle
5,240,995 A 8/1993 Gyory et al.
5,254,346 A 10/1993 Tucker et al.
5,270,358 A 12/1993 Asmus
5,276,079 A 1/1994 Duan et al.
5,296,512 A 3/1994 Beier et al.
5,300,291 A 4/1994 Sablotsky et al.
5,310,563 A 5/1994 Curtis et al.
5,322,689 A 6/1994 Hughes et al.
5,326,685 A 7/1994 Gaglio et al.
5,332,576 A 7/1994 Mantelle
5,338,490 A 8/1994 Dietz et al.
5,342,623 A 8/1994 Enscore et al.
5,344,394 A 9/1994 Gyory et al.
5,354,823 A 10/1994 Tseng et al.
5,362,420 A 11/1994 Itoh et al.
5,376,377 A 12/1994 Gale et al.
5,422,119 A 6/1995 Casper
5,438,076 A 8/1995 Friedman et al.
5,446,070 A 8/1995 Mantelle
5,456,745 A 10/1995 Roreger et al.
5,462,743 A 10/1995 Turner et al.
5,462,745 A 10/1995 Enscore et al.
5,492,943 A 2/1996 Stempel
5,508,024 A 4/1996 Tranner
5,508,367 A 4/1996 Zajaczkowski
5,527,271 A 6/1996 Shah et al.
5,543,148 A 8/1996 Lapidus
5,563,153 A 10/1996 Mueller et al.
5,575,654 A 11/1996 Fontenot
5,593,686 A 1/1997 Kissel et al.
5,594,068 A 1/1997 Buchanan et al.
5,599,373 A 2/1997 Zanuccoli
5,614,178 A 3/1997 Bloon et al.
5,631,267 A 5/1997 Gleich et al.
5,633,010 A 5/1997 Chen
5,641,504 A 6/1997 Lee et al.
5,641,507 A 6/1997 DeVillez
5,643,187 A 7/1997 Næstoft et al.
5,645,062 A 7/1997 Anderson et al.
5,645,855 A 7/1997 Lorenz
5,656,286 A 8/1997 Miranda et al.
5,660,178 A 8/1997 Kantner et al.
5,662,925 A 9/1997 Ebert et al.
5,663,010 A 9/1997 Stocchiero
5,674,561 A 10/1997 Dietz et al.
5,700,478 A 12/1997 Biegajski et al.
5,702,721 A 12/1997 Horstmann et al.
5,718,187 A 2/1998 Pollock et al.
5,718,886 A 2/1998 Pellico
5,719,197 A 2/1998 Kanios et al.
5,723,145 A 3/1998 Shikinami et al.
5,725,876 A 3/1998 Mantelle et al.
5,726,250 A 3/1998 Zajaczkowski
5,730,999 A 3/1998 Lehmann et al.
5,744,155 A 4/1998 Friedman et al.
5,762,956 A 6/1998 Chien
5,770,220 A 6/1998 Meconi et al.
5,773,490 A 6/1998 Shikinami et al.
5,780,050 A 7/1998 Jain et al.
5,785,527 A 7/1998 Jensen et al.
5,785,976 A 7/1998 Westesen et al.
5,788,983 A 8/1998 Chien et al.
5,800,832 A 9/1998 Tapolsky et al.
5,804,611 A 9/1998 Takoh et al.
5,827,213 A 10/1998 Jensen
5,827,525 A 10/1998 Liao et al.
5,830,932 A 11/1998 Kay
5,837,713 A 11/1998 Gliech et al.
5,843,472 A 12/1998 Ma et al.
5,846,558 A 12/1998 Nielsen et al.
5,851,549 A 12/1998 Svec
5,853,755 A 12/1998 Foldvari
5,858,332 A 1/1999 Jensen et al.
5,858,410 A 1/1999 Muller et al.
5,863,662 A 1/1999 Hornby et al.
5,876,746 A 3/1999 Jona et al.
5,879,691 A 3/1999 Sagel et al.
5,879,701 A 3/1999 Audett et al.
5,891,453 A 4/1999 Sagel et al.
5,894,017 A 4/1999 Sagel et al.
5,900,249 A 5/1999 Smith
5,902,598 A 5/1999 Chen et al.
5,911,980 A 6/1999 Samour et al.
5,912,271 A 6/1999 Brodin et al.
5,916,587 A 6/1999 Min et al.
5,942,543 A 8/1999 Ernst
5,945,032 A 8/1999 Breitenbach et al.
5,945,457 A 8/1999 Plate et al.
5,948,416 A 9/1999 Wagner et al.
5,948,430 A 9/1999 Zerbe et al.
5,948,433 A 9/1999 Burton et al.
5,958,379 A 9/1999 Regenold et al.
5,958,446 A 9/1999 Miranda et al.
5,958,984 A 9/1999 Devillez
5,962,011 A 10/1999 DeVillez
5,972,377 A 10/1999 Jona et al.
5,976,565 A 11/1999 Fotinos
5,985,311 A 11/1999 Cordes et al.
5,985,860 A 11/1999 Toppo
5,985,990 A 11/1999 Kantner et al.
5,989,569 A 11/1999 Dirksing et al.
5,990,179 A 11/1999 Gyory et al.
5,993,836 A 11/1999 Castillo
5,993,849 A 11/1999 Assmus et al.
5,997,886 A 12/1999 Peffly et al.
6,004,566 A 12/1999 Friedman et al.
6,004,578 A 12/1999 Lee et al.
6,007,837 A 12/1999 Enscore et al.
6,024,976 A 2/2000 Miranda et al.
6,045,811 A 4/2000 Dirksing et al.
6,051,609 A 4/2000 Yu et al.
6,063,399 A 5/2000 Assmus et al.
6,068,650 A 5/2000 Hofmann et al.
6,072,100 A 6/2000 Mooney et al.
6,075,626 A 6/2000 Mizutani et al.
6,083,421 A 7/2000 Huang et al.
6,093,328 A 7/2000 Santina

(56) References Cited

U.S. PATENT DOCUMENTS

| | | | |
|---|---|---|---|
| 6,096,328 | A | 8/2000 | Sagel et al. |
| 6,135,126 | A | 10/2000 | Joshi |
| 6,142,939 | A | 11/2000 | Eppstein et al. |
| 6,146,654 | A | 11/2000 | Kubo |
| 6,153,215 | A | 11/2000 | Samuelsen et al. |
| 6,162,456 | A | 12/2000 | Dunbar et al. |
| 6,165,499 | A | 12/2000 | Kleinsorgen et al. |
| 6,177,096 | B1 | 1/2001 | Zerbe et al. |
| 6,193,993 | B1 | 2/2001 | Murahashi et al. |
| 6,197,331 | B1 | 3/2001 | Lerner et al. |
| 6,201,164 | B1 | 3/2001 | Wulff et al. |
| 6,212,671 | B1 | 4/2001 | Kanehira et al. |
| 6,221,341 | B1 | 4/2001 | Montgomery |
| 6,221,383 | B1 | 4/2001 | Miranda et al. |
| 6,231,885 | B1 | 5/2001 | Carrara |
| 6,248,363 | B1 | 6/2001 | Patel et al. |
| 6,264,981 | B1 | 7/2001 | Zhang et al. |
| 6,270,792 | B1 | 8/2001 | Guillemet et al. |
| 6,275,728 | B1 | 8/2001 | Venkatraman et al. |
| 6,306,370 | B1 | 10/2001 | Jensen et al. |
| 6,312,666 | B1 | 11/2001 | Oxman et al. |
| 6,312,670 | B1 | 11/2001 | Montgomery |
| 6,316,022 | B1 | 11/2001 | Mantelle et al. |
| 6,322,774 | B1 | 11/2001 | Jensen et al. |
| 6,329,472 | B1 | 12/2001 | Kim et al. |
| 6,368,576 | B1 | 4/2002 | Jensen et al. |
| 6,419,905 | B1 | 7/2002 | Alvarez Hernandez |
| 6,419,906 | B1 | 7/2002 | Xu et al. |
| 6,451,240 | B1 | 9/2002 | Sherman et al. |
| 6,451,777 | B1 | 9/2002 | Bradbury et al. |
| 6,461,636 | B1 | 10/2002 | Arth et al. |
| 6,488,913 | B2 | 12/2002 | Orlowski et al. |
| 6,517,350 | B2 | 2/2003 | Diasti et al. |
| 6,552,147 | B2 | 4/2003 | Parker et al. |
| 6,558,654 | B2 | 5/2003 | McLaughlin |
| 6,562,363 | B1 | 5/2003 | Mantelle et al. |
| 6,576,712 | B2 | 6/2003 | Feldstein et al. |
| 6,585,997 | B2 | 7/2003 | Moro et al. |
| 6,591,124 | B2 | 7/2003 | Sherman et al. |
| 6,596,298 | B2 | 7/2003 | Leung et al. |
| 6,602,912 | B2 | 8/2003 | Hsu et al. |
| 6,611,706 | B2 | 8/2003 | Avrahami et al. |
| 6,638,528 | B1 | 10/2003 | Kanios |
| 6,656,493 | B2 | 12/2003 | Dzija |
| 6,667,410 | B2 | 12/2003 | Magnus et al. |
| 6,673,363 | B2 | 1/2004 | Luo et al. |
| 6,682,721 | B2 | 1/2004 | Kim et al. |
| 6,689,344 | B2 | 2/2004 | Chang et al. |
| 6,696,459 | B1 | 2/2004 | Jones et al. |
| 6,708,060 | B1 | 3/2004 | Avrahami et al. |
| 6,709,671 | B2 | 3/2004 | Zerbe et al. |
| 6,711,435 | B2 | 3/2004 | Avrahami |
| 6,714,497 | B2 | 3/2004 | Yeo et al. |
| 6,750,291 | B2 | 6/2004 | Kim et al. |
| 6,759,030 | B2 | 7/2004 | Kosti |
| 6,762,202 | B2 | 7/2004 | Marek et al. |
| 6,780,401 | B2 | 8/2004 | Kim et al. |
| 6,783,769 | B1 | 8/2004 | Arth et al. |
| 6,803,420 | B2 | 10/2004 | Cleary et al. |
| 6,805,874 | B1 | 10/2004 | Lutz et al. |
| 6,806,308 | B2 | 10/2004 | Zajac |
| 6,884,833 | B2 | 4/2005 | Cheang et al. |
| 6,946,142 | B2 | 9/2005 | Chang et al. |
| 6,962,691 | B1 | 11/2005 | Lulla et al. |
| 7,078,359 | B2 | 7/2006 | Stepanian et al. |
| 7,112,713 | B2 | 9/2006 | Sceusa |
| 7,122,199 | B2 | 10/2006 | Sagel et al. |
| 7,138,458 | B2 | 11/2006 | Cleary et al. |
| 7,217,853 | B2 | 5/2007 | Kulichikhin et al. |
| 7,323,161 | B2 | 1/2008 | Choi et al. |
| 7,384,650 | B2 | 6/2008 | Chien |
| 7,456,331 | B2 | 11/2008 | Kulichikhin et al. |
| 7,744,918 | B2 | 6/2010 | Yamaguchi et al. |
| 8,206,738 | B2 | 6/2012 | Singh et al. |
| 8,273,405 | B2 | 9/2012 | Feldstein et al. |
| 8,481,059 | B2 | 7/2013 | Cleary et al. |
| 8,481,071 | B2 | 7/2013 | Singh et al. |
| 2001/0006677 | A1 | 7/2001 | Mcginity et al. |
| 2001/0021374 | A1 | 9/2001 | Montgomery |
| 2001/0046471 | A1 | 11/2001 | Marek et al. |
| 2002/0004190 | A1 | 1/2002 | Diasti et al. |
| 2002/0009420 | A1 | 1/2002 | McLaughlin |
| 2002/0048602 | A1 | 4/2002 | Flore et al. |
| 2002/0076487 | A1 | 6/2002 | Zajac |
| 2002/0106335 | A1 | 8/2002 | Orlowski et al. |
| 2002/0131990 | A1 | 9/2002 | Barkalow et al. |
| 2002/0197284 | A1 | 12/2002 | Luo et al. |
| 2003/0035841 | A1 | 2/2003 | Dzija |
| 2003/0055190 | A1 | 3/2003 | Parker et al. |
| 2003/0068376 | A1 | 4/2003 | Chen et al. |
| 2003/0100654 | A1 | 5/2003 | Cheang et al. |
| 2003/0101507 | A1 | 6/2003 | Cleary et al. |
| 2003/0103427 | A1 | 6/2003 | Yeo et al. |
| 2003/0104041 | A1 | 6/2003 | Hsu et al. |
| 2003/0152528 | A1 | 8/2003 | Singh et al. |
| 2003/0152615 | A1 | 8/2003 | Houze et al. |
| 2003/0170308 | A1 | 9/2003 | Cleary et al. |
| 2003/0180229 | A1 | 9/2003 | Kosti |
| 2003/0225356 | A1 | 12/2003 | Kulichikhin et al. |
| 2003/0235549 | A1 | 12/2003 | Singh et al. |
| 2004/0005277 | A1 | 1/2004 | Willison et al. |
| 2004/0053901 | A1 | 3/2004 | Chien |
| 2004/0105834 | A1 | 6/2004 | Singh et al. |
| 2004/0136927 | A1 | 7/2004 | Kim et al. |
| 2004/0166147 | A1 | 8/2004 | Lundy et al. |
| 2004/0219111 | A1 | 11/2004 | Kim et al. |
| 2004/0258723 | A1 | 12/2004 | Singh et al. |
| 2005/0031554 | A1 | 2/2005 | Kim et al. |
| 2005/0113510 | A1 | 5/2005 | Feldstein et al. |
| 2005/0208110 | A1 | 9/2005 | Singh et al. |
| 2005/0215727 | A1 | 9/2005 | Feldstein et al. |
| 2005/0228113 | A1 | 10/2005 | Baumer et al. |
| 2005/0256223 | A1 | 11/2005 | Kolb et al. |
| 2006/0034905 | A1 | 2/2006 | Singh et al. |
| 2006/0110434 | A1 | 5/2006 | Yamaguchi et al. |
| 2006/0168905 | A1 | 8/2006 | Blanc et al. |
| 2006/0171906 | A1 | 8/2006 | Singh et al. |
| 2006/0182788 | A1 | 8/2006 | Singh et al. |
| 2006/0193793 | A1 | 8/2006 | Kim et al. |
| 2006/0193794 | A1 | 8/2006 | Kim et al. |
| 2008/0161492 | A1 | 7/2008 | Cleary et al. |
| 2009/0155343 | A1 | 6/2009 | Kawahara et al. |
| 2009/0258060 | A1 | 10/2009 | Cleary et al. |
| 2012/0027695 | A1 | 2/2012 | Feldstein et al. |
| 2012/0237579 | A1 | 9/2012 | Singh et al. |
| 2012/0321569 | A1 | 12/2012 | Feldstein et al. |

FOREIGN PATENT DOCUMENTS

| | | | |
|---|---|---|---|
| CA | 2451431 | | 1/2003 |
| CA | 2506073 | | 6/2004 |
| CA | 2579492 | | 3/2006 |
| DE | 8509793 | | 5/1985 |
| DE | 4219368 | | 6/1992 |
| DE | 4219368 | | 12/1993 |
| EP | 0184470 | | 6/1986 |
| EP | 0303445 | | 2/1989 |
| EP | 0364211 | | 4/1990 |
| EP | 0371421 | | 6/1990 |
| EP | 0511782 | | 11/1992 |
| EP | 0516026 | | 12/1992 |
| EP | 0545594 | | 6/1993 |
| EP | 0581581 | | 2/1994 |
| EP | 0672094 | | 9/1995 |
| EP | 0737477 | | 10/1996 |
| EP | 0838225 | | 4/1998 |
| EP | 0848960 | | 6/1998 |
| EP | 1066823 | | 1/2001 |
| EP | 2005952 | A1 | 12/2008 |
| GB | 1108837 | | 4/1968 |
| JP | 58-162681 | | 9/1983 |
| JP | 59-196817 | | 11/1984 |
| JP | 01-151524 | A | 6/1989 |
| JP | 03-066612 | | 3/1991 |

(56) References Cited

FOREIGN PATENT DOCUMENTS

| | | | |
|---|---|---|---|
| JP | 03-247334 | | 5/1991 |
| JP | 03-275619 | | 6/1991 |
| JP | 04-266818 | | 9/1992 |
| JP | 06-100467 | | 4/1994 |
| JP | 10-017448 | | 1/1998 |
| JP | 2001-213768 | A | 7/2001 |
| JP | 2002-029949 | | 1/2002 |
| JP | 2002-145746 | A | 5/2002 |
| KR | 20020045224 | | 6/2002 |
| KR | 20030000299 | | 1/2003 |
| KR | 20030000528 | | 1/2003 |
| KR | 20030003969 | | 1/2003 |
| KR | 20030003973 | | 1/2003 |
| SU | 1459215 | | 11/1995 |
| WO | WO 89/03859 | | 5/1989 |
| WO | WO 93/02717 | | 5/1989 |
| WO | WO 99/07940 | A1 | 7/1990 |
| WO | WO 94/05340 | | 3/1994 |
| WO | WO 96/19205 | | 6/1996 |
| WO | WO 97/11676 | | 4/1997 |
| WO | WO 98/20862 | A1 | 5/1998 |
| WO | WO 98/26763 | A1 | 6/1998 |
| WO | WO 98/37870 | | 9/1998 |
| WO | WO 98/55044 | | 12/1998 |
| WO | WO 99/11728 | A1 | 3/1999 |
| WO | WO 99/17738 | | 4/1999 |
| WO | WO 99/44678 | | 9/1999 |
| WO | WO 99/47128 | | 9/1999 |
| WO | WO 99/54422 | | 10/1999 |
| WO | WO 99/55312 | A2 | 11/1999 |
| WO | WO 00/16725 | | 3/2000 |
| WO | WO 00/18365 | A2 | 4/2000 |
| WO | WO 00/61120 | A1 | 10/2000 |
| WO | WO 00/69421 | | 11/2000 |
| WO | WO 01/01958 | A1 | 1/2001 |
| WO | WO 01/07018 | A1 | 2/2001 |
| WO | WO 01/26637 | | 4/2001 |
| WO | WO 01/68045 | | 9/2001 |
| WO | WO 01/87276 | | 11/2001 |
| WO | WO 02/00182 | A3 | 1/2002 |
| WO | WO 02/04570 | | 1/2002 |
| WO | WO 02/43657 | A2 | 6/2002 |
| WO | WO 02/087642 | | 11/2002 |
| WO | WO 02/087645 | | 11/2002 |
| WO | WO 02/089849 | | 11/2002 |
| WO | WO 03/000216 | | 1/2003 |
| WO | WO 03/011259 | A1 | 2/2003 |
| WO | WO 03/089046 | | 10/2003 |
| WO | WO 03/099344 | | 12/2003 |
| WO | WO 03/101357 | A1 | 12/2003 |
| WO | WO 2004/045569 | | 6/2004 |
| WO | WO 2004/054638 | | 7/2004 |
| WO | WO 2004/071323 | | 8/2004 |
| WO | WO 2004/093786 | | 11/2004 |
| WO | WO 2004/103201 | | 12/2004 |
| WO | WO 2005/027768 | | 3/2005 |
| WO | WO 2005/074894 | A1 | 8/2005 |
| WO | WO 2006/017807 | | 2/2006 |
| WO | WO 2006/029407 | | 3/2006 |
| WO | WO 2006/069236 | | 6/2006 |
| WO | WO 2006/074173 | | 7/2006 |
| WO | WO 2006/081497 | | 8/2006 |
| WO | WO 2006/124639 | | 11/2006 |
| WO | WO 2007/119656 | | 10/2007 |
| WO | WO 2010/083035 | | 7/2010 |

OTHER PUBLICATIONS

International Search Report or PCT/US/2006/000098 Mailed Nov. 3, 2006.

International Search Report for PCT/US2006/0003091 Mailed Oct. 11, 2006.

International Search Report for PCT/US2006/018500 Mailed Sep. 21, 2006.

International Search Report for PCT/US2010/000081 Mailed Sep. 7, 2010.

Schehlmann "Polyvinylcaprolactam: physical and cosmetic properties of a new hair fixative resin", Lecture held at the In-Cosmetics, SOFW-Journal-Sounderdruck, Dusseldorf, 6 pages (1997).

Whelan Polymer Technology Dictionary, Citation Butyl Rubber, Chapman Hall, 2-6 Boundry Row, London, UK, vol. 1, pp. 53 (1994).

Aubin et al., "Analysis of the glass transition temperature of miscible polymer blends", Macromolecules, vol. 21, pp. 2945-2949, (1988).

Bairamov et al., "Kinetic parameters of poly(N-vinyl pyrrolidone) spontaneous mixing with short-chain poly(ethylene glycol)", Polym. Mater. Sci. Eng., vol. 82, pp. 7-8, (2000).

Borodulina et al. "Viscoelasticity of Pressure-sensitive adhesive and bioadhesive hydrogels under compressive load", Proceed. 24th Annual Meeting Adhesion Soc., pp. 147-149, (2001).

Chalykh et al., "Effects of composition and hydration on adhesive properties of poly(N-vinyl pyrrolidone)-poly(ethylene glycol) hydrogels", Polym. Mater. Sci. Eng., vol. 81, pp. 456-457, (1999).

Chalykh et al., "Fracture mechanics of poly(N-vinyl pyrrolidone)-poly(ethylene glycol) hydrogel adhesive joints," Polym. Mater. Sci. Eng., vol. 81, pp. 427-428, (1999).

Chalykh et al., "Pressure-sensitive adhesion in the blends of poly(N-vinyl pyrrolidone) and poly(ethylene glycol) of disparate chain lengths," J. Adhesion, vol. 78, pp. 667-694, (2002).

Cleary et. al., A new polymer blend adhesive with combined properties to adhere to either skin or mucosa for drug delivery, podium abstract, 30th Annual Meeting and Exposition of the Controlled Release Society, Glasgow, Scotland, Jul. 19-23, 2003, Abstract #123.

Database WPI Section Ch, Week 198451, Derwent Publications Ltd., London, GB; Class A96, AN 1984-315114 & JP 59196817 A (Sekisuki Chem Ind Co Ltd) Nov. 8, 1984 abstract.

Database WPI Section Ch, Week 199150, Derwent Publications Ltd., London, GB; Class A18, AN 1991-366353 & JP 03247334 A (Sumitomo Rubber Ind Ltd) Nov. 5, 1991 abstract.

Database WPI Section Ch, Week 199118, Derwent Publications Ltd., London, GB; Class A96, AN 1991-128478 & JP 03066612 A (Sato Pharm Co Ltd) Mar. 22, 1991 abstract.

Database WPI Section Ch, Week 199627, Derwent Publications Ltd., London, GB; Class A14, AN 1996-266746 & SU 1459215 A ( A Med Cardiology Res Centre) Nov. 20, 1995 abstract.

Emla Cream, (lidocaine 2.5% and prilocaine 2.5%), Emla Anesthetic Disc, (lidocaine 2.5% and prilocaine 2.5% cream), "Topical anesthetic for dermal analgesia", AstraZeneca Product Monograph, 46 pgs, Revised May 25, 2010.

Feldstein et al., "A structure—property relationship and quantitative approach to the development of universal transdermal drug delivery system," NBC Risks, vol. 25, pp. 441-458, (1999).

Feldstein et al., "Coherence of thermal transitions in poly(N-vinyl pyrrolidone)-poly(ethylene glycol) compatible blends: 1. Interrelations among the temperatures of melting, maximum cold crystalization rate and glass transition", Polymer, vol. 41, pp. 5327-5338, (2000).

Feldstein et al., "Coherence of thermal transitions in poly(N-vinyl pyrrolidone)-poly(ethylene glycol) compatible blends: 2. The temperature of maximum cold crystalization rate versus glass transition", Polymer, vol. 41, pp. 5339-5348, (2000).

Feldstein et al., "Coherence of thermal transitions in poly(N-vinyl pyrrolidone)-poly(ethylene glycol) compatible blends: 3. Impact of sorbed water upon phase behavior", Polymer, vol. 41, pp. 5349-5359, (2000).

Feldstein et al., "Correlations between activation energy for debonding and that for self-diffusion in pressure-sensitive hydrogels", Proceed. 24th Annual Meeting Adhesion Soc., pp. 137-140, (2001).

Feldstein et al., "Contribution of molecular mobility to debonding of pressure-sensitive adhesive hydrogels", Polym. Mater. Sci. Eng., vol. 81, pp. 467-468, (1999).

Feldstein et al., "Effect of hydrophilic matrix hydration on transdermal drug delivery kinetics: I. The matrix hydration In Vivo and In Vitro", Prediction of Percutaneous Penetration, vol. 4b, pp. 61-64, Brian, et al., (Eds.) (1996).

(56) References Cited

OTHER PUBLICATIONS

Feldstein et al., "Effect of hydrophilic matrix hydration on transdermal drug delivery kinetics: II. In Vitro cytasine Delivery From Cypercuten TTS", Prediction of Percutaneous Penetration, vol. 4b, pp. 65-67, Brian, et al., (Eds.) (1996).
Feldstein et al., "Effect of hydrophilic matrix hydration on transdermal drug delivery kinetics: III. In Vitro clonide delivery from clopercuten TTS", Prediction of Percutaneous Penetration, vol. 4b, pp. 68-70, Brian, et al., (Eds.) (1996).
Feldstein et al., "Effect of hydrophilic matrix hydration on transdermal drug delivery kinetics: IV. In Vitro—In Vivo correlation," Prediction of Percutaneous Penetration, vol. 4b, pp. 71-73, Brian, et al., (eds.) (1996).
Feldstein et al., "Effects of chains orientation, free volume and interaction on glass transition in poly(N-vinyl pyrrolidone)—poly(ethylene glycol) blends involving a stoichiometric hydrogen-B bonded network complex", Polym. Mater. Sci. Eng., vol. 82, pp. 365-366, (2000).
Feldstein et al., "General approach to the molecular design of hydrophilic pressure-sensitive adhesives," Proc. 25th Ann. Mtg. and 2nd World Congress on Adhesion and Related Phenomena, Orlando, FL, vol. 1, pp. 292-294 (2002).
Feldstein et al., "Molecular insight into rheological and diffusion determinants of pressure sensitive adhesion", Proceed. 23rd Annual Meeting Adhesion Soc., pp. 54-56, (2000).
Feldstein et al., "Peculiarities of glass transition temperature relation to the composition of poly(N-vinyl pyrolidone) blends with short chain poly(ethylene glycol)", Polymer, vol. 42, pp. 7719-7726, (2001).
Feldstein et al., "Quantitative relationship between molecular structure and adhesion of PVP-PEG hydrogels", Polym. Mater. Sci Eng., vol. 81, pp. 465-466, (1999).
Feldstein et al., "Relation of glass transition temperature to the hydrogen bonding degree and energy in poly(N-vinyl pyrrolidone) blends with hydroxyl-containing plasticizers: 2. Effects of poly(ethylene glycol) chain length", Polymer, vol. 42, pp. 981-990, (2001).
Feldstein et al., "Universal hydrophilic drug-containing adhesive matrix for systemic and topical transdermal drug delivery", Proc. 1st World Meeting APGI/APV, Budapest, 9/11, 2 pages, (1995).
Handbook of Pharmaceutical Excipients, Arther H. Kibbe, ed., 3rd ed., pp. 401-406, (2000).
Hawley's Condensed Chemical Dictionary, 14th Edition, Citation, "Oligomer, a polymer molecule of only a few monomer units (dimer, trimer, tetramer)", John Wiley and Sons, Inc., (2002).
International Search Report for PCT/US2000/18557 mailed Oct. 17, 2000.
International Search Report for PCT/US2001/21417 mailed Feb. 25, 2002.
International Search Report for PCT/US2002/13680 mailed Sep. 18, 2002.
International Search Report for PCT/US2002/14260 Mailed Sep. 17, 2002.
International Search Report for PCT/US2002/14725 mailed Sep. 27, 2002.
International Search Report for PCT/US2003/16408 Mailed Dec. 8, 2003.
International Search Report for PCT/US2003/039717 Mailed Jun. 28, 2004.
International Search Report for PCT/US2004/003443 Mailed Aug. 20, 2004.
International Search Report for PCT/US2004/011567 Mailed Jan. 10, 2006.
International Search Report for PCT/US2004/015448 Mailed Dec. 28, 2004.
International Search Report for PCT/US2004/029620 Mailed Jun. 1, 2005.
International Search Report for PCT/US2005/0002873 Mailed Apr. 27, 2005.
Kotomin et al., "Squeeze-recoil analysis of adhesive hydrogels and elastomers", Polym. Mater. Sci. Eng., vol. 81, pp. 425-426, (1999).
Kotomin et al., "Durability and fracture of some visceolastic adhesives," Proceed. Of The 23rd Annual Meeting Of The Adhesion Soc., pp. 413-415, (Feb. 20-23, 2000).
MSDS (Material Safety Data Sheet), Lactic Acid, No. L0522, (2008).
Patent Abstracts of Japan, vol. 017, No. 055 (C-I023) Feb. 3, 1993 & JP 04 266818 A (Sekisui Chem Co Ltd), Sep. 22, 1992 abstract.
Roos et al., "Probe tack investigation of poly(vinyl pyrrolidone)-poly(ethylene glycol) blends", Proceed. 24th Annual Meeting Adhesion Soc., pp. 277-279, (2001).
Sintov et al., "Radiofrequency-driven skin microchanneling as a new way for electically assisted transdermal delivery of hydrophilic drugs", J. Contr.Release, vol. 89, pp. 311-320, (2003).
Supplementary European Search Report for EP04783729.9 Mailed Jun. 5, 2009.
Vartapian et al., "Self-diffusion in poly(N-vinyl pyrrolidone)-poly-(ethylene glycol) systems", Colloid Polym. Sci., vol. 279, pp. 532-538, (2001).
Vartapian et al., "Molecular dynamics in poly(N-vinyl pyrrolidone)-poly(ethylene glycol) blends by pulsed-field gradient NMR method: effects of aging, hydration and PEG chain length", Macromol. Chem. Phys., vol. 202, pp. 2648-2652, (2001).
Borodulina et al. (2001), "Viscoelasticity of Pressure-Sensitive Adhesive and Bioadhesive Hydrogels Under Compressive Load," *Proceed. 24th Annual Meeting Adhesion Soc.,* pp. 147-149.
Aubin (1988), "Analysis of the Glass Transition Temperature of Miscible Polymer Blends," *Macromolecules* 21:2945-2949.
Bairamov et al. (2000), "Kinetic Parameters of Poly(N-Vinyl Pyrrolidone) Spontaneous Mixing with Short-Chain Poly(Ethylene Glycol)," *Polym. Mater. Sci. Eng.* 82:7-8.
Chalykh et al. (1999), "Effects of Composition and Hydration on Adhesive Properties of Poly(N-Vinyl Pyrolidone)—Poly(Ethylene Glycol) Hydrogels," *Polym. Mater. Sci. Eng* 81:456-457.
Feldstein et al. (1995), "Universal Hydrophilic Drug-Containing Adhesive Matrix for Systemic and Topical Transdermal Drug Delivery," *Proc. 1st World Meeting APGI/APV,* Budapest, 9/11.
Feldstein et al. (1996), "Effect of Hydrophilic Matrix Hydration on Transdermal Drug Delivery Kinetics: I. The Matrix Hydration In Vivo and In Vitro," *Prediction of Percutaneous Penetration* 4b:61-64, Brain et al. (Eds).
Feldstein et al. (1999), "A Structure-Property Relationship and Quantitative Approach to the Development of Universal Transdermal Drug Delivery System," *NBC (Nuclear, Biological, and Chemical) Risks—Current Capabilities and Future Perspectives for Protection* 25:441-458, Kluwer Academic Purlbishers, Netherlands, NATO Science Series: 1. Disarmament Technologies.

PREPARATION OF HYDROPHILIC PRESSURE SENSITIVE ADHESIVES HAVING OPTIMIZED ADHESIVE PROPERTIES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

[This application] *More than one reissue application has been filed for the reissue of U.S. Pat. No. 6,576,712. The reissue applications are the present application and application Ser. No. 11/150,811, now U.S. Reissue Pat. No. RE44145. The present application is a continuation reissue of application Ser. No. 11/150,811, now U.S. Reissue Pat. No. RE44145, which is an application for reissue of U.S. Pat. No. 6,576,712. U.S. Pat. No. 6,576,712* is a continuation-in-part of U.S. patent application Ser. No. 09/847,532, filed May 1, 2001, *now abandoned,* which [claimed] *claims* priority under 35 U.S.C. §119(e)(1) to U.S. Provisional Patent Application No. 60/216,386, filed Jul. 7, 2000.

TECHNICAL FIELD

This invention relates to preparation of adhesive compositions. More particularly, the invention relates to preparation of hydrophilic pressure sensitive adhesive (PSA) compositions having optimized adhesive properties and that are useful, for example, in transdermal drug delivery systems and other medical, pharmaceutical and cosmetic products that adhere to the skin or other body surface. The invention has utility in a number of fields, including transdermal drug delivery, iontophoretic systems, biomedical electrode fabrication, wound healing, and skin care and cosmetic products.

BACKGROUND

Pressure-sensitive adhesives are well known and have been used for many years in a variety of industrial, consumer and medical applications. Pressure-sensitive adhesives are characterized as being normally tacky and exhibiting instant tack when applied to a substrate. Many polymers have been used to manufacture pressure sensitive adhesives as, for example, acrylic and methacrylic ester homo- or copolymers, butyl rubber-based systems, silicones, urethanes, vinyl esters and amides, olefin copolymer materials, natural or synthetic rubbers, and the like. All the PSAs are elastomers, i.e. they exhibit viscoelastic properties typical of rubbers.

Pressure sensitive adhesives are used extensively in transdermal drug delivery devices, or "patches," that adhere to the skin or mucosal tissue during use. Adhesive, transport, reservoir and biological properties of polymeric composites constitute a basis for their application in transdermal drug delivery systems, as follows:

Adhesive: High tack coupled with an optimum slip-stick transition point.

Transport: Drug release kinetics controlled in terms of transdermal delivery rate and the functional lifetime of device.

Reservoir: Drug compatibility and ability to be stored in a stable form tailored to the incorporated drug of interest.

Biological: No toxicity, skin irritation and sensitization.

Such diverse requirements are difficult to combine in a single system.

Examples of pressure sensitive adhesives that have been proposed for use in transdermal drug delivery systems include polysiloxanes (e.g., polydimethyl siloxanes, polydiphenyl siloxanes, and siloxane blends), polyisobutylenes, polyacrylates, acrylic acid-acrylate copolymers (e.g., copolymers of acrylic acid copolymers with 2-ethylhexyl acrylate or isooctyl acrylate), and tacky rubbers such as polyisobutene, polybutadiene, polystyrene-isoprene copolymers, polystyrene-butadiene copolymers, and neoprene (polychloroprene). All of these PSAs are hydrophobic polymers and their common disadvantage is a loss in adhesion toward hydrated substrates.

"Bioadhesion" is defined as a pressure sensitive adhesion with respect to highly hydrated biological tissues such as mucosal tissue. In contrast to conventional PSAs (rubber, polysiloxanes and acrylates) that adhere mainly to dry substrates, bioadhesives (BAs) exhibit good tack when adhered to hydrated biological substrates. To be bioadhesive, water should provide a plasticizing effect on a polymer, i.e., the polymer should be hydrophilic. For example, the range of typical BAs includes slightly crosslinked polyacrylic and polymethacrylic acids (EP 0371 421) as well as blends of hydrophilic cellulose derivatives (40-95%) with polyethylene glycol (PEG) (U.S. Pat. No. 4,713,243).

Bioadhesives become tacky as the crosslinked polymer swells in significant quantities of water. The cohesive strength of highly swollen hydrophilic polymers is generally low and the BAs thus differ from the PSAs in this regard.

For a number of practical purposes, it can be highly useful to have a range of PSA and BA polymeric materials of different hydrophilicity and thus different solubilities in water or in the liquids secreted by the skin and mucosa (sweat, mucus, saliva etc.). Attempts to combine the properties of PSAs and BAs have been described by Biegajski et al. in U.S. Pat. No. 5,700,478, where a water-soluble pressure-sensitive mucoadhesive was obtained by blending of 95-40% polyvinylpyrrolidone (PVP) with 0-50% hydroxypropyl cellulose (HPC) and 11-60% glycerol. Other examples of hydrophilic polymer blends coupling the properties of PSAs and BAs involve polyacrylic acid-polyvinyl alcohol (PAA-PVA) interpolymeric complexes formed by hydrogen bonding between the monomer units of the complementary polymers chains and plasticized with PEG-200, glycerol or polypropylene glycol (PPG), molecular weight 425 g/mol (German Patent Application DE 42 19 368).

The ideal performance characteristics of an adhesive intended for use on human skin and/or mucosal tissue present difficult and conflicting technical requirements. Initially, of course, the pressure sensitive adhesive should be suitable for long-term skin contact, and permeable to and physically and chemically compatible with the active agent and any permeation enhancers or other vehicles or additives that are present. The ideal adhesive should also be nonirritating, noncomedogenic and nonsensitizing, yet bond quickly to skin or mucosal tissue at the intended site of use with only very slight pressure. The adhesive should maintain its bond for as long a period of time as necessary and be resistant to inadvertent removal, yet be easily removed without removing any skin or leaving a residue (a suitable strength of an adhesive joint with the skin ranges from about 200 to 400 N/m under the 180 degree peel test). High tack (i.e., greater than about 50 g/cm$^2$) should be coupled with an optimum transition point from adhesive to cohesive failure. Furthermore, the adhesive should not be weakened or destroyed by exposure to moisture or high humidity. Finally, in order to protect a wound or maintain the integrity of placement of an electrode or other device, the adhesive should resist skin movement and be able to transfer a mechanical load from the adhesive backing to the skin.

For many pharmaceuticals, the solubility of the active agent in the reservoir of a transdermal drug delivery device is of decisive importance. With higher solubility, it is possible to increase the rate of transdermal delivery (i.e., the rate at which the active agent migrates from the device and into the skin or mucosal tissue). Because many therapeutic agents are ionogenic organic substances having a higher solubility in hydrophilic media than in lipophilic media, adhesive reservoirs based on hydrophilic polymers would be more versatile than adhesive reservoirs based on hydrophobic polymers. Furthermore, as noted above, pressure sensitive adhesives for application to mucosal tissue should adhere well to hydrated substrates, and hydrophilic adhesives would therefore be ideal.

General advantages of hydrophilic adhesives are as follows:

1. Hydrophilic adhesives can provide greater adhesion compared with hydrophobic adhesives, because the surface energy of hydrophilic adhesives is typically higher and closer to that of biological substrates such as skin and mucosal membranes.
2. Hydrophilic adhesives are compatible with a wide variety of drugs, excipients and additives.
3. The plasticizing effect of water sorbed by hydrophilic adhesives from hydrated skin or mucosal tissues enhances adhesion, in contrast to hydrophobic adhesives.
4. The enhanced solubility of drugs in hydrophilic adhesives facilitates control over drug release kinetics.
5. With hydrophilic adhesives, based on hydrophilic polymers, there is an expanded capability to control and manipulate the adhesive-cohesive balance.
6. The adhesive properties of hydrophilic polymers are considerably less sensitive to their molecular weight than those of hydrophobic polymers, as a result of specific intramolecular and intermolecular interaction within hydrophilic adhesives.

In order to increase the hydrophilicity of an adhesive composition, hydrophobic PSAs have been "hydrophilized" by incorporation of non-tacky hydrophilic polymers and fillers into a hydrophobic adhesive. Thus, polyisobutylene (PIB) PSA has been hydrophilized by incorporation of cellulose and cellulose derivatives (U.S. Pat. No. 4,231,369), polyvinyl alcohol (PVA), pectin and gelatin (U.S. Pat. Nos. 4,367,732 and 4,867,748), and $SiO_2$ (U.S. Pat. No. 5,643,187). Rubber adhesives have also been modified by filling with amphiphilic surfactants, or by treating the PSA polymer with a plasma-oxygen discharge. Acrylic PSAs can be hydrophilized by incorporation of PVP (U.S. Pat. No. 5,645,855). Hydrophilization of hydrophobic adhesives, while somewhat effective, tends to result in a partial loss of adhesion.

Accordingly, there is a need in the art for a novel hydrophilic adhesive composition suitable for use in a wide variety of contexts, e.g., in a topically applied drug delivery system, which composition meets all of the above criteria and provides for an effective delivery rate of any active agent, whether hydrophilic, ionogenic, or lipophilic in nature.

The present invention is addressed to the aforementioned need in the art, and enables the development of a wide range of hydrophilic pressure-sensitive adhesives that not only meet all of the aforementioned criteria but provide other advantages as well. For example, the adhesive compositions combine the properties of pressure-sensitive adhesives and bioadhesives and can be used in a number of contexts, including not only transdermal, transmucosal and topical drug delivery systems but also in wound healing products, biomedical electrodes, iontophoretic systems, bioadhesive cushions, and the like. Also, the adhesive compositions can be used with a number of active agents, regardless of hydrophilicity, hydrophobicity, and molecular structure. Manufacture of adhesive products using the present compositions is readily accomplished by a simple extrusion process, obviating the need for organic solvents and the conventional, time-consuming blending and casting method. Finally, the adhesive composition may be readily tailored during manufacture with respect to hygroscopicity, the desired degree of hydrophilicity, adhesive and cohesive strength, and drug delivery kinetics.

SUMMARY OF THE INVENTION

It is thus a primary object to address the above-described need in the art by providing a method for making hydrophilic pressure sensitive adhesive compositions useful in transdermal drug delivery systems, iontophoretic systems, wound healing products, biomedical electrodes, and other devices and systems requiring a bioadhesive.

It is another object of the invention to provide a hydrophilic pressure sensitive adhesive that is optimized with respect to adhesive strength, cohesive strength and hydrophilicity.

It is another object of the invention to provide a therapeutic system for the topical or transdermal administration of a pharmacologically active agent, wherein the system is provided with an adhesive means comprised of a hydrophilic pressure sensitive adhesive composition as provided herein.

Additional objects, advantages and novel features of the invention will be set forth in part in the description which follows, and in part will become apparent to those skilled in the art upon examination of the following, or may be learned by practice of the invention.

In one aspect of the invention, then, a method is provided for preparing an adhesive composition having an optimized degree of adhesion, comprising:

(a) preparing a plurality of compositions each comprised of a hydrophilic polymer having a glass transition temperature $T_{g\ pol}$ admixed with a plasticizer having a glass transition temperature $T_{g\ pl}$ and capable of covalently or noncovalently crosslinking the hydrophilic polymer, wherein the weight fraction of the hydrophilic polymer in each composition is $w_{pol}$, and the weight fraction of the plasticizer in each composition is $w_{pl}$;

(b) calculating predicted glass temperatures $T_{g\ predicted}$ for each composition using the Fox equation (1)

$$\frac{1}{T_{g\ predicted}} = \frac{w_{pol}}{T_{g_{pol}}} + \frac{w_{pl}}{T_{g_{pl}}} \tag{1}$$

and plotting $T_{g\ predicted}$ versus $w_{pl}$, for each composition;

(c) determining the glass transition temperature $T_{g\ actual}$ for each composition, and plotting $T_{g\ actual}$ versus $w_{pl}$, for each composition;

(d) identifying the region of the plots of (b) and (c) wherein $T_{g\ actual}$ is less than $T_{g\ predicted}$; such that there is a negative deviation from $T_{g\ predicted}$;

(e) within the region identified in (d), identifying the optimum weight of plasticizer $w_{pl\ optimum}$ at which the negative deviation from $T_{g\ predicted}$ is at a maximum; and (f) admixing a monomeric precursor to the hydrophilic polymer and the plasticizer under polymerizing conditions to provide an adhesive composition having an optimized degree of adhesion, wherein the weight fraction of plasticizer in the composition is $w_{pl\ optimums}$ and the weight fraction of the hydrophilic polymer in the composition is $1-w_{pl\ optimum}$.

In some cases, e.g., when a lower degree of adhesion is desired, the selected weight percent of the plasticizer will not correspond to the maximum negative deviation of $T_{g\ actual}$ from $T_{g\ predicted}$, but will correspond to some other predetermined deviation of $T_{g\ actual}$ from $T_{g\ predicted}$. Accordingly, in another aspect of the invention, a method is provided for preparing an adhesive composition having a predetermined degree of adhesion, comprising:

(a) preparing a plurality of compositions each comprised of a hydrophilic polymer having a glass transition temperature $T_{g\ pol}$ admixed with a plasticizer having a glass transition temperature $T_{g\ pl}$ and capable of covalently or noncovalently crosslinking the hydrophilic polymer, wherein the weight fraction of the hydrophilic polymer in each composition is $w_{pol}$, and the weight fraction of the plasticizer in each composition is $w_{pl}$, such that $w_{pol}$ is equal to $1-w_{pl}$;

(b) calculating predicted glass temperatures $T_{g\ predicted}$ for each composition using the Fox equation (1)

$$\frac{1}{T_{g\ predicted}} = \frac{w_{pol}}{T_{g_{pol}}} + \frac{w_{pl}}{T_{g_{pl}}} \quad (1)$$

and plotting $T_{g\ predicted}$ versus $w_{pl}$ for each composition;

(c) determining the glass transition temperature $T_{g\ actual}$ for each composition, and plotting $T_{g\ actual}$ versus $w_{pl}$ for each composition;

(d) identifying the region of the plots of (b) and (c) wherein $T_{g\ actual}$ has a predetermined deviation from $T_{g\ predicted}$; and (e) admixing a monomeric precursor to the hydrophilic polymer and the plasticizer under polymerizing conditions to provide an adhesive composition having a predetermined degree of adhesion, wherein the weight percent of plasticizer in the composition corresponds to a value within the region identified in section (d).

In another aspect of the invention, a hydrophilic pressure sensitive adhesive composition is provided that comprises (1) a hydrophilic polymer having a glass transition temperature $T_{g\ pol}$, and (2) a complementary hydroxyl-terminated or carboxyl-terminated short-chain plasticizing agent having a glass transition temperature $T_{g\ pl}$ and capable of hydrogen bonding or electrostatic bonding to the hydrophilic polymer, wherein the weight ratio of hydrophilic polymer to complementary short-chain plasticizing agent is selected so to provide a predetermined deviation in (a) the actual glass transition temperature $T_{g\ actual}$ of the composition from (b) the predicted glass transition temperature $T_{g\ predicted}$ calculated for the composition using the Fox equation. For maximum adhesion, the predetermined deviation is the maximum negative deviation of $T_{g\ actual}$ from $T_{g\ predicted}$. Preferably, the difference between $T_{g\ pol}$ and $T_{g\ pl}$ is at least about 50° C., such that $T_{g\ actual}$ for each composition is determined solely by $T_{g\ pl}$.

In related aspects of the invention, a hydrophilic pressure sensitive adhesive composition is provided that comprises (a) a hydrophilic polymer, and (b) a complementary hydroxyl-terminated or carboxyl-terminated short-chain plasticizing agent capable of hydrogen bonding or electrostatic bonding to the hydrophilic polymer, wherein the ratio of hydrogen bonding to covalent crosslinks and/or the ratio of the hydrophilic polymer to the plasticizing agent are selected to optimize the hydrophilicity, adhesive strength and cohesive strength of the composition.

In a further aspect of the invention, a drug delivery system is provided for the topical or transdermal administration of a pharmacologically active agent. The drug delivery system includes:

(A) a drug reservoir comprising (1) a substantially non-aqueous pressure sensitive adhesive matrix of a hydrophilic polymer having a glass transition temperature $T_{g\ pol}$, and a complementary hydroxyl-terminated or carboxyl-terminated short-chain plasticizing agent having a glass transition temperature $T_{g\ pl}$ and capable of hydrogen bonding or electrostatic bonding to the hydrophilic polymer, wherein the weight ratio of hydrophilic polymer to complementary short-chain plasticizing agent is selected so to provide a predetermined deviation in (a) the actual glass transition temperature $T_{g\ actual}$ of the composition from (b) the predicted grass transition temperature $T_{g\ predicted}$ for the composition calculated using the Fox equation, and (2) a therapeutically effective amount of the active agent; and (B) a backing layer laminated to the drug reservoir that serves as the outer surface of the device during use.

The adhesive compositions herein are also useful in a host of additional applications, e.g., in bandages, wound and burn dressings, ostomy devices, prosthesis securing means, face masks, sound, vibration or impact absorbing materials, and the like. The compositions may be rendered electrically conductive by incorporation of water and/or another electrically conductive material, and may thus be used for attaching an electroconductive article, such as an electrode (e.g., a transcutaneous electric nerve stimulation, or "TENS" electrode, an electrosurgical return electrode or an EKG monitoring electrode), to an individual's body surface.

DETAILED DESCRIPTION OF THE INVENTION

Figure 1:
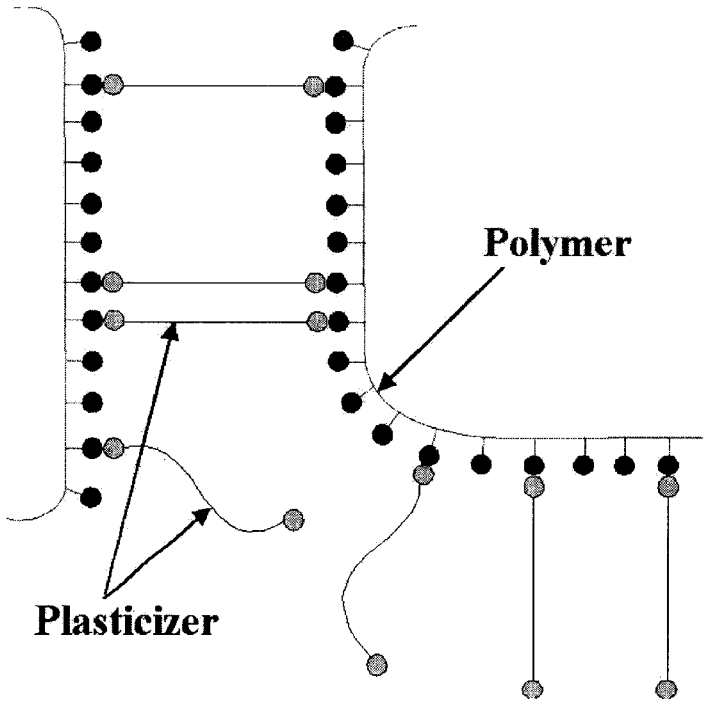
FIG. 1 represents a schematic view of the molecular design of a hydrogen-bonded or electrostatic-bonded network complex formed by a long-chain hydrophilic polymer and a short-chain plasticizer.

Before describing the present invention in detail, it is to be understood that unless otherwise indicated this invention is not limited to specific therapeutic agents, polymeric materials, drug delivery devices, or the like, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a hydrophilic polymer" includes a mixture of two or more such polymers, reference to "a cross-linking agent" includes mixtures of two or more cross-linking agents, and the like.

In describing and claiming the present invention, the following terminology will be used in accordance with the definitions set out below.

The terms "active agent," "drug," and "therapeutic agent" are used interchangeably herein to refer to a chemical material or compound suitable for transdermal or transmucosal administration and which induces a desired effect. The terms include agents that are therapeutically effective, prophylactically effective, or cosmetically effective. Also included are derivatives and analogs of those compounds or classes of compounds specifically mentioned which also induce the desired effect.

By "transdermal" drug delivery is meant administration of a drug to the skin surface of an individual so that the drug passes through the skin tissue and into the individual's blood stream. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

The term "topical administration" is used in its conventional sense to mean delivery of an active agent to the skin or mucosa, as in, for example, topical drug administration in the prevention or treatment of various skin disorders, the application of cosmetics and cosmeceuticals (including moisturizers, masks, sunscreens, etc.), and the like. Topical administration, in contrast to transdermal administration, provides a local rather than a systemic effect.

The term "body surface" is used to refer to skin or mucosal tissue, including the interior surface of body cavities that have a mucosal lining. The term "skin" should be interpreted as including "mucosal tissue" and vice versa.

Similarly, when the term "transdermal" is used herein, as in "transdermal drug administration" and "transdermal drug delivery systems," it is to be understood that unless explicitly indicated to the contrary, both "transmucosal" and "topical" administration and systems are intended as well.

"Hydrophobic" polymers and "hydrophilic" polymers are defined herein as suggested by Zaikov et al. (1987), "Diffusion of electrolytes in polymers," VSP (Utrecht—Tokyo). It is based on the amount of water vapor absorbed by polymers at 100% relative humidity. According to this classification, the hydrophobic polymers absorb only up to 1 wt. % water at 100% relative humidity ("rh"), while the moderately hydrophilic polymer absorbs 1-10% wt. % of water at 100% rh. Hydrophilic polymers are capable of sorbing more than 10 wt. % of water, while hygroscopic polymers sorb more than 20 wt. % of water.

The term "crosslinked" herein refers to a composition containing intramolecular and/or intermolecular crosslinks, whether arising through covalent or noncovalent bonding. "Noncovalent" bonding includes hydrogen bonding, electrostatic (ionic) bonding, and absorption.

The terms "tack" and "tacky" are qualitative. However, the terms "substantially nontacky" "slightly tacky" and "tacky," as used herein, may be quantified using the values obtained in a PKI or TRBT tack determination method, as follows. By "substantially nontacky" is meant a composition that has a tack value that is less than about 25 g-cm/sec, by "slightly tacky" is meant a composition that has a tack value in the range of about 25 g-cm/sec to about 100 g-cm/sec, and by "tack" is meant a hydrogel that has a tack value of at least 100 g-cm/sec.

Unless otherwise indicated, all molecular weight values given herein are weight average molecular weights.

In a first embodiment, the invention provides a method for obtaining hydrophilic PSAs by mixing a specific amount of a selected hydrophilic polymer with a specific amount of a selected complementary short-chain plasticizer capable of hydrogen bonding to the hydrophilic polymer. Suitable hydrophilic polymers include repeating units derived from an N-vinyl lactam monomer, a carboxy vinyl monomer, a vinyl ester monomer, an ester of a carboxy vinyl monomer, a vinyl amide monomer, and/or a hydroxy vinyl monomer. Such polymers include, by way of example, poly(N-vinyl lactams), poly(N-vinyl acrylamides), poly(N-alkylacrylamides), substituted and unsubstituted acrylic and methacrylic acid polymers, polyvinyl alcohol (PVA), polyvinylamine, copolymers thereof and copolymers with other types of hydrophilic monomers (e.g. vinyl acetate).

Poly(N-vinyl lactams) useful herein are preferably non-crosslinked homopolymers or copolymers of N-vinyl lactam monomer units, with N-vinyl lactam monomer units representing the majority of the total monomeric units of a poly (N-vinyl lactams) copolymer. Preferred poly(N-vinyl lactams) for use in conjunction with the invention are prepared by polymerization of one or more of the following N-vinyl lactam monomers: N-vinyl-2-pyrrolidone; N-vinyl-2-valerolactam; and N-vinyl-2-caprolactam. Nonlimiting examples of non-N-vinyl lactam comonomers useful with N-vinyl lactam monomeric units include N,N-dimethylacrylamide, acrylic acid, methacrylic acid, hydroxyethylmethacrylate, acrylamide, 2-acrylamido-2-methyl-1-propane sulfonic acid or its salt, and vinyl acetate.

Poly (N-alkylacrylamides) include, by way of example, poly(methacrylamide) and poly(N-isopropyl acrylamide) (PNIPAM).

Polymers of carboxy vinyl monomers are typically formed from acrylic acid, methacrylic acid, crotonic acid, isocrotonic acid, itaconic acid and anhydride, a 1,2-dicarboxylic acid such as maleic acid or fumaric acid, maleic anhydride, or mixtures thereof, with preferred hydrophilic polymers within this class including polyacrylic acid and polymethacrylic acid, with polyacrylic acid most preferred.

Preferred hydrophilic polymers herein are the following: poly(N-vinyl lactams), particularly polyvinyl pyrrolidone (PVP) and poly(N-vinyl caprolactam) (PVC); poly(N-vinyl acetamides), particularly polyacetamide per se; polymers of carboxy vinyl monomers, particularly polyacrylic acid and polymethacrylic acid; and copolymers and blends thereof. PVP and PVC are particularly preferred.

The molecular weight of the hydrophilic polymer is not critical; however, the weight average molecular weight of the hydrophilic polymer is generally in the range of approximately 100,000 to 2,000,000, more typically in the range of approximately 500,000 to 1,500,000. The hydrophilic polymer may or may not be adhesive in nature, as a nonadhesive hydrophilic polymer will become adhesive upon admixture with a predetermined quantity of the plasticizing agent.

The complementary short-chain plasticizing agent is terminated with hydroxyl groups, amino or carboxyl groups, and is typically a monomeric or oligomeric material that has a glass transition temperature $T_g$ in the range of about −100° C. to about −30° C. and a melting temperature $T_m$ lower than about 20° C. The plasticizing agent may be also amorphous. The difference between the $T_g$ values of polymer and plasticizer has a decisive significance for the adhesive behavior of the polymer-plasticizer blend. Preferably, the difference is greater than about 50° C., preferably greater than about 100° C., and most preferably in the range of about 150° C. to about 300° C. The hydrophilic polymer and complementary short-chain plasticizer should be compatible, i.e. capable of forming a homogeneous blend that exhibits a single $T_g$, intermediate between those of the unblended components. Generally, the plasticizing agent will have a molecular weight in the range from about 45 to about 800, preferably in the range of about 45 to about 600. Examples of suitable plasticizing agents include, but are not limited to, low molecular weight polyalcohols (e.g. glycerol), monomeric or oligoalkylene glycols such as ethylene glycol and propylene glycol, ether alcohols (e.g., glycol ethers), alkane diols from butane diol to octane diol includingly, carboxyl-terminated and amino-terminated derivatives of polyalkylene glycols such as polyethylene glycol, and carbonic diacids. Polyalkylene glycols, optionally carboxyl-terminated, are preferred herein, and polyethylene glycol having a molecular weight in the range of about 300 to 600 is an optimal plasticizing agent.

The hydrophilic polymer and plasticizer should be miscible with respect to each other and have disparate chain lengths (as may be deduced from the above). The ratio of the weight average molecular weight of the hydrophilic polymer to that of the short-chain plasticizer should be within about 200 and 200,000, preferably within about 1,250 and 20,000. Also, the polymer and the plasticizer should contain complementary functional groups capable of hydrogen bonding or electrostatic bonding to each other. Ideally, the complementary functional groups of the polymer are located throughout the polymeric structure, while the functional groups of the plasticizer are preferably located at the two termini of a linear molecule, and are not present along the backbone, if the plasticizer is a polymer or an oligomer. Forming hydrogen bonds or ionic bonds between the two terminal functional groups of the plasticizer and the corresponding functional groups contained along the backbone of the hydrophilic polymer results in a noncovalently linked supramolecular network structure outlined in simplified view in FIG. 1. Strong interaction between the complementary groups of the plasticizer and hydrophilic polymer imparts cohesive strength to the network. At the same time, due to the length and flexibility of the plasticizer molecules, they behave as spacers, creating a free volume between cohesively interacting macromolecules of the hydrophilic polymer. In this way, the apparently conflicting performance properties of pressure-sensitive adhesives are both achieved: a liquid-like fluidity needed for adhesive bonding, coupled with a rubber-like resistance to shear deformation necessary to dissipate the detaching energy under adhesive joint failure.

In addition, the plasticizer has been found to decrease the glass transition temperature of the hydrophilic polymer/plasticizer composition to a greater degree than predicted by the Fox equation, which is given by equation (1)

$$\frac{1}{T_{g\,predicted}} = \frac{w_{pol}}{T_{g_{pol}}} + \frac{w_{pl}}{T_{g_{pl}}} \tag{1}$$

where $T_{g\,predicted}$ is the predicted glass transition temperature of the hydrophilic polymer/plasticizer composition, $w_{pol}$ is the weight fraction of the hydrophilic polymer in the composition, $w_{pl}$ is the weight fraction of the plasticizer in the composition, $T_{g\,pol}$ is the glass transition temperature of the hydrophilic polymer, and $T_{g\,pl}$ is the glass transition temperature of the plasticizer. The inventors herein have now discovered that an adhesive composition having an optimized (e.g., maximized) degree of adhesion can be prepared from a hydrophilic polymer and a complementary plasticizer by selecting the components and their relative amounts to give a predetermined deviation from $T_{g\,predicted}$, even if each component individually is non-tacky. Generally, the predetermined deviation from $T_{g\,predicted}$ will be the maximum negative deviation, such that this is the point where adhesive strength is maximized.

Figure 2:
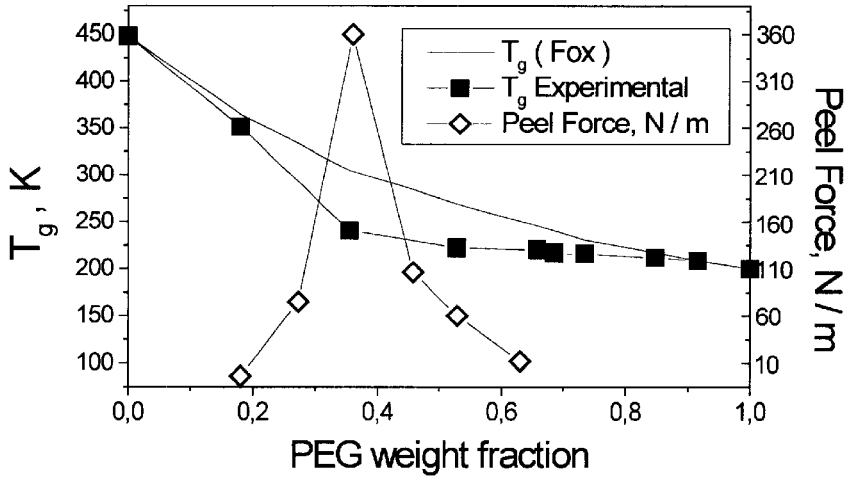
FIG. 2 is a graph illustrating the adhesion characteristics of a PVP-PEG (m.w. 400 g/mole) blend, evaluated in terms of the 180° peel force needed to rupture an adhesive bond with a polyethylene (PE) substrate at a debonding rate of 10 mm/min, with respect to the compositional behavior of the glass transition temperature, $T_g$, in the blend. The points denote experimental data, whereas the line connecting the $T_g$s of PVP and PEG-400 was obtained using the Fox equation.

That is, the weight ratio of hydrophilic polymer to plasticizer should be of a specified value in order for adhesion to appear in a blend of a non-tacky hydrophilic polymer and a short-chain complementary plasticizer. As FIG. 2 illustrates, in PVP blends with PEG-400 adhesion is inherent only in those compositions that demonstrate negative deviations from the $T_g$ value predicted by the Fox equation (1). The larger the negative deviation, the higher the adhesion. This finding is generally applicable and is not limited to PVP-PEG-400 blends. Preferably, the negative deviation is within the range about 30° C. to about 150° C., preferentially from about 50° C. to about 120° C. The extent of the negative $T_g$ deviation depends on the difference between the $T_g$s of blend components, i.e., between $T_{g\,pol}$ and $T_{g\,pl}$. In general, the negative $T_g$ deviation should be approximately 20-40% of the difference between the $T_g$ values of unblended polymer and plasticizer.

Figure 3:
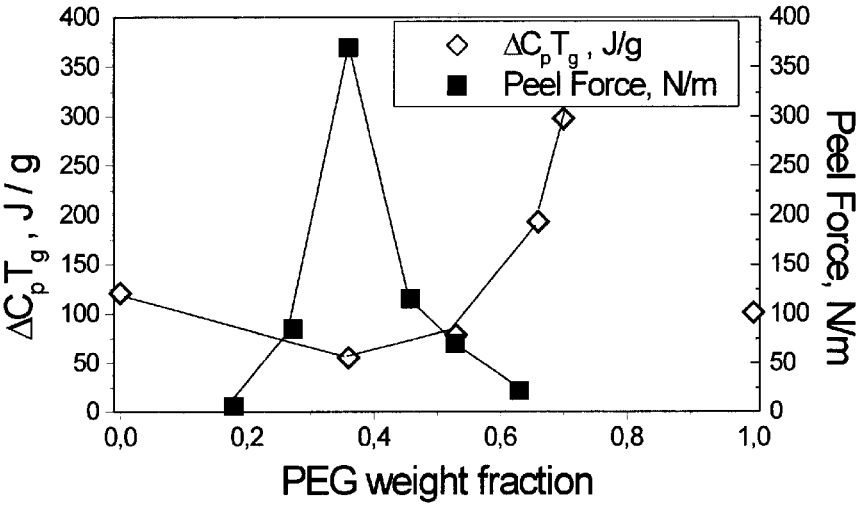
FIG. 3 is a plot of $\Delta C_p T_g$ against the composition of PVP blends with PEG-400.

Another general predictor of pressure-sensitive adhesive behavior in polymers is the $\Delta C_p T_g$ product, where $\Delta C_p$ is the change in heat capacity at the polymer transition point from the glassy to the viscoelastic state. This product features a measure of the amount of heat that has to be expended in order to provide the polymer transition from the glassy to the viscoelastic state and to impart translational mobility to polymeric segments. As PVP mixing with PEG-400 occurs, the $\Delta C_p T_g$ product decreases, passing through a minimum that corresponds to the maximum in blend adhesion (FIG. 3). It is the product $\Delta C_p T_g$ which sets the PSAs apart from non-adhesive polymers (Table 1). The $\Delta C_p T_g$ values, which are associated with the adhesive PVP-PEG blends and hydrophobic PSA's (PDMS, PIB and natural rubber), are notably grouped within a narrow area ranging from 45.0 to 92.0 J/g, predominantly near 65-80 J/g. Non-adhesive polymers exhibit higher $\Delta C_p T_g$ values.

TABLE 1

Glass transition characteristics of representative polymers.

| Polymer | Tg, K | ΔCp, J/gK | ΔCpTg J/g |
|---|---|---|---|
| Polydimethylsiloxane | 150 | 0.30 | 45.0 |
| Polyisobuthylene | 200 | 0.40 | 79.6 |
| Natural rubber | 200 | 0.46 | 92.0 |
| Polyethylene | 237 | 0.39 | 92.5 |
| PEG - 400 | 200 | 0.51 | 101.4 |
| Bisphenol polycarbonate | 415 | 0.25 | 103.9 |
| Polymethyl methacrylate | 385 | 0.29 | 112.8 |
| Poly(N-vinyl pyrrolidone) | 449 | 0.27 | 121.2 |
| Polypropylene | 253 | 0.55 | 139.2 |
| Polystyrene | 375 | 0.38 | 141.0 |
| Polyvinyl acetate | 305 | 0.50 | 153.4 |
| Polyethylene terephthalate | 340 | 0.49 | 165.7 |
| Polyvinyl chloride | 355 | 0.63 | 229.9 |

The $\Delta C_p T_g$ value outlines a subtle balance between free volume and cohesive interactions energy in polymers (Feldstein et al. (1999), Polym Mater. Sci. Eng. 81:467-468). In general, the enhanced free volume has to be counterbalanced by a high attractive interaction energy in order for adhesion to appear. Enhanced free volume results in high molecular mobility and liquid-like fluidity of a PSA polymer, whereas substantial cohesive interaction energy provides cohesive toughness and rubber-like resistance to flow.

As the actual glass transition temperature $T_{g\ actual}$ for the present adhesive compositions will generally be substantially lower than that predicted by the Fox equation, particularly since the composition of preferred adhesives herein is selected to correspond to the maximum negative deviation of $T_{g\ actual}$ from $T_{g\ predicted}$, the heat required to transform a glassy polymer blend to a viscoelastic composition is minimal.

When reduced to the most basic molecular level, all performance properties of polymeric materials are interrelated through the structure and interaction of the involved macromolecules. This is also the case for the interrelationship between the diffusivity and tack of pressure-sensitive adhesives. As has been recently shown (Feldstein et al. (2000), Proceed. 23rd Annual Meeting Adhesion Soc., pp. 54-56), with a cohesive type of adhesive debonding (which is typical of various PSA polymers and polymeric blends) the peel force P necessary to rupture the adhesive bond, P, relates to a self-diffusion coefficient of a PSA polymer segment, D, by equation (2):

$$P = b \cdot l \frac{a \cdot N \cdot \tau \cdot D}{12RT} \sigma_f^2 \tag{2}$$

where b is the width and l the thickness of the adhesive layer, a is a size of diffusing polymer segment, N is Avogadro's number, $\tau$ is a segmental relaxation time and $\sigma_f$ is a critical stress at adhesive polymer fracture under detaching tensile force. Equation (2) establishes a general relation of adhesive strength to the measures of molecular mobility (D) and cohesive toughness ($\sigma_f$) of PSA polymer.

While not wishing to be bound by theory, the inventors herein believe that equation (2) explains why adhesion goes through a maximum upon mixing a hydrophilic polymer with a short-chain plasticizer bearing complementary reactive functional groups at the chain ends. Forming hydrogen or electrostatic bonds through both terminal groups of the plasticizer provides noncovalent crosslinking of the hydrophilic polymer chains into a supramolecular network structure of a polymer blend. Due to the considerable length and flexibility of plasticizer chains, the network structure provides enhanced free volume and molecular mobility coupled with high cohesive strength, i.e. the properties governing the adhesive behavior of polymer blends. With the increase in plasticizer concentration the molecular mobility (D) increases, whereas the cohesive strength ($\sigma_f$) follows the opposite pattern. For this reason, lower ratios (i.e., a lower relative amount of hydrophilic polymer) results in a liquid or semi-liquid composition, while higher ratios (i.e., a higher relative amount of hydrophilic polymer) gives a rise to a high cohesive strength material. High cohesive strength can in turn cause a deterioration in mechanical properties and, with drug delivery systems, can also lower the rate of drug release.

Figure 4:
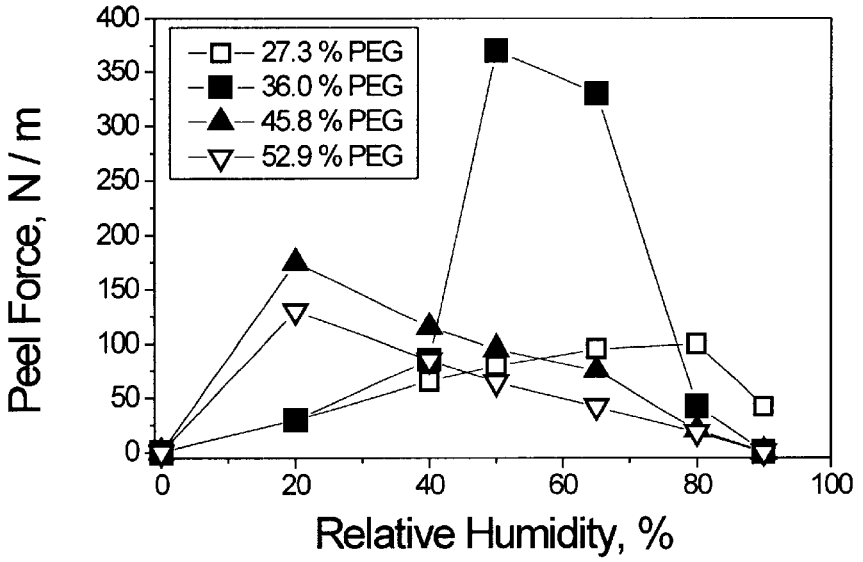
FIG. 4 shows the effects of the plasticizer-hydrophilic polymer ratio and the relative humidity of the surrounding atmosphere on the adhesion of PVP plasticized with PEG-400, evaluated in terms of 180° peel force.
Figure 5:
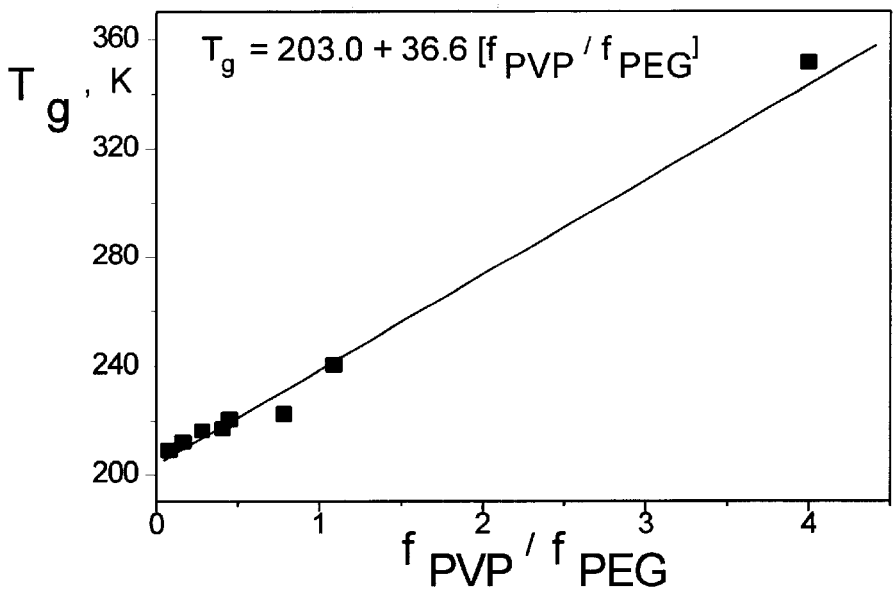
FIG. 5 represents the Kovacs plot for miscible PVP-PEG blends.

As is evident from the data in FIG. 4, water absorption causes opposite effects on the adhesion of blends of hydrophilic polymers underloaded with a short-chain telechelic plasticizer (27.3%) and overloaded with such plasticizer (45.8 and 52.9%). Water vapour absorption is associated with a significant plasticizing action of water as reflected by a significant reduction in glass transition temperature of hydrophilic polymer. The left-hand (ascending) branch of the curves in FIG. 3 correspond to compositions in the immediate vicinity of the glass transition, and water behaves there as a plasticizer by promoting the transition of the PSA into a viscoelastic state and enhancing adhesion. By contrast, for rubbery blends in the right-hand (descending) branches of the plot, water serves as a cosolvent and contributes to the reduction of adhesive toughness by decreasing the cohesive strength of hydrogels (equation (2)). In this way, by varying the ratio of the plasticizer to the hydrophilic polymer, a composition may be transformed from bioadhesive to pressure-sensitive adhesive.

The PVP-PEG system is considered here as a model, but it is to be understood that the invention is not limited in this regard, and a number of hydrophilic polymers and plasticizers may be substituted for PVP and PEG, respectively. The broad applicability of the invention results primarily from the properties of the plasticizers rather than those of the hydrophilic polymers. This fundamental conclusion has also a theoretical confirmation. As is evident from Examples 1-67, a specific type of compositional behavior of the blend $T_g$, outlined by both the negative deviations from the weight-average magnitudes obtained with the Fox equation (1), $-\Delta T_g$, and the $\Delta C_p T_g$ quantity, is a factor controlling adhesion. Over the years, numerous equations have been proposed to express the $T_g$-composition dependence of miscible polymer blends and plasticized systems (see Aubin (1988), Prud'homme R. E. "Analysis of the glass transition temperature of miscible polymer blends," Macromolecules 21:2945-2949). In general, it is observed, that $T_g$ varies monotonically as a function of composition demonstrating a rapid initial reduction followed by a gradual leveling off the response as a plasticizer is added. The difference between measured $T_g$ values and those predicted with relevant equations is usually considered a measure of the strength of interactions between molecules of the involved components. The Kovacs equation (3) holds if the difference in $T_g$ between the glass transition temperature of a PEG plasticizer component and the glass transition temperature of a PVP polymer (and between any miscible hydrophilic polymer and complementary plasticizer) is larger than about 50° C.:

$$T_g = T_{gPEG} + \frac{f_{gPVP}}{\Delta\alpha_{PEG}} \cdot \frac{\phi_{PVP}}{\phi_{PEG}} \tag{3}$$

where $f_g$ is the fractional free volume of PVP at $T_g$, $\Delta\alpha$ is the thermal expansion coefficient for PEG and $\phi$ is polymer volume fraction in the blend. The $f_g$ factor has been found to be of the same universal magnitude, about 0.025, for all polymers (see Ferry (1970). Viscoelastic Properties of Polymers, 2nd Ed., Wiley: N.Y., Chapter 11). The Kovacs equation (3) manifests theoretically that the specific behavior of a PVP-PEG system is due to the PEG properties. Actually, no other factors relating to PVP, except for the universal $f_g$ value (which, again, is of a common magnitude for different polymers), control the blend $T_g$. Thus, the validity of the Kovacs equation for the PVP-PEG system implies that the difference between the $T_g$s of a hydrophilic polymer and a short-chain complementary plasticizer should be larger than 50° C. in order for pressure-sensitive adhesion to appear upon blending the polymer and plasticizer.

Equation (3) indicates also that for every given short-chain telechelic plasticizer, the blend composition that corresponds to the maximum negative deviation in $T_{g\ actual}$ from $T_{g\ predicted}$ and, consequently, to the maximum adhesion, is practically unaffected by the structure of the higher-$T_g$ hydrophilic complementary polymer. In other words, if the highest degree of adhesive strength appears in PVP-PEG blends at a PEG concentration of 36 wt. %, PEG blends with other complementary hydrophilic polymers will also exhibit the maximum degree of adhesion in vicinity of 36 wt. % plasticizer, providing that the $T_g$ of the hydrophilic polymer is more than 50° C. higher than the $T_g$ of the plasticizer.

The hydrophilic polymer and the plasticizing agent are blended in a ratio designed to optimize adhesive and cohesive strength as well as hydrophilicity and thus, in drug delivery systems, the kinetics of drug delivery. The ratio is as discussed above, i.e., a preferred weight ratio of hydrophilic polymer to plasticizer should be in the range defined by the maximum values of the negative $T_g$ deviations from the weight-average magnitudes calculated using the Fox equation (1) or outlined by the minimum values of the $\Delta C_p T_g$ criterion (FIGS. 2 and 3).

The free volume and cohesive energy of polymer compositions have to be in a specified ratio in order for a composition to exhibit pressure-sensitive adhesion. See Feldstein et al. (1999), "Quantitative relationship between molecular structure and adhesion of PVP-PEG hydrogels," Polym. Mater. Sci. Eng. 81:465-466; Feldstein et al. (1999), "Contribution of molecular mobility to debonding of pressure sensitive adhesive hydrogels," Polym. Mater. Sci. Eng. 81:465-466; Feldstein et al. (1999), "A structure—property relationship and quantitative approach to the development of universal transdermal drug delivery system," in: T. Sohn and V. A. Voicu (eds.), NBC (Nuclear Biological, and Chemical) Risks—Current Capabilities and Future Perspectives for Protection, Kluwer Academic Publishers, NATO Science Series: 1. Disarmament Technologies, vol. 25, Dordrecht-Boston-London, (1999), pp. 441-458; and Feldstein et al. (2000), "Molecular insight into Theological and diffusion determinants of pressure sensitive adhesion," Proceed. 23rd Annual Meeting Adhesion Soc. 2000, pp. 54-56.

Generally, for high adhesion, substantial cohesive interactions have to be counterbalanced by a large free volume. The energy of cohesive interactions in adhesive gels is controlled by both the hydrophilic polymer/short-chain plasticizer ratio and the crosslinker/hydrophilic polymer ratio. As a measure of adhesion, the durability of adhesive joints under fixed detaching force, t* (sec), may be employed, using a squeeze-recoil test described by Kotomin et al. (2000), "Durability and fracture of some viscoelastic adhesives," Proceed. 23rd Annual Meeting Adhesion Soc., pp. 413-415. A longer period of durability indicates a higher degree of adhesion in terms of a conventional peel test.

The composition may or may not be hydrated, depending on the desired use. For example, transdermal and transmucosal drug delivery systems will generally contain zero to about 7 wt. % water, while products such as facial masks, electroconductive adhesive products, cosmeceutical products, topical pharmaceutical formulations, and other products in which a gel type adhesive (i.e., a hydrogel adhesive) is desired, will generally contain about 7 wt. % to about 40 wt. % water. The optimum degree of hydration depends on the nature and hygroscopic of the hydrophilic polymer and the short-chain plasticizer. For example, an optimum PVP-PEG-400 system for most uses will contain from 2 to 20 wt. % of residual water, preferably from 2 to 12 wt. % water, most preferably between 6 and 10 wt. % water. It will be appreciated that the rise in plasticizer hygrosopicity with the decrease in PEG chain length leads to an increase in the degree of optimum hydration, whereas the replacement of highly hygrosopic PVP with less hygrosopic PVCap results in the decrease of hydration providing best adhesion. However, some hydration will occur upon application of the adhesive composition to skin or other body surface. In some cases, it may be desirable to add water or an organic solvent such as ethanol to the adhesive composition prior to use, so as to generate a hydrogel. A hydrogel may be advantageous in a number of contexts.

The compositions are self-adhesive and normally do not require the addition of tackifiers. However, other additives may be incorporated into the present adhesive compositions, so long as they are not detrimental to the composition in any way. For example, the following optional components are often present in adhesive formulations and are presented here for illustrative purposes only and are not meant to limit the adhesive compositions in any way. These optional components include including fillers, chain transfer agents for controlling molecular weight (e.g., carbon tetrabromide, mercaptans, or alcohols), pigments, dyes, refractive particles, preservatives, stabilizers, toughening agents, antimicrobial agents (e.g., mercurochrome, silver sulfadiazine, povidine iodine, iodine), cosmetic agents (e.g., glycerine, urea, allantoin, sulfur, anthraquinone, hydroquinones), moisturizers, humectants, anesthetics (e.g., benzocaine), healing agents (e.g., collagen), and the like. Insoluble fibrous fillers may be advantageously incorporated to control the degree of hydration when the adhesive is on the skin or other body surface. Such fillers can include cellulosic materials as described in International Patent Publication No. WO 89/03859, e.g., woven and non-woven paper and cotton materials. Other suitable fillers are inert, i.e., substantially non-adsorbent, and include, for example, polyethylenes, polypropylenes, polyurethane polyether amid copolymers, polyesters and polyester copolymers, nylon and rayon. These additives, and amounts thereof, are selected in such a way that they do not significantly interfere with polymerization, crosslinking or the desired chemical and physical properties of the final adhesive.

The adhesive compositions may be rendered electrically conductive for use in biomedical electrodes and other electrotherapy contexts, i.e., to attach an electrode or other electrically conductive member to the body surface. For example, the adhesive compositions may be used to attach a transcutaneous nerve stimulation electrode, an electrosurgical return electrode, or an EKG electrode to a patient's skin or mucosal tissue. Generally, these applications involve modification of the adhesive composition so as to contain a conductive species, thereby rendering the adhesive composition as a whole conductive. Suitable conductive species include the ionically conductive electrolytes that are commonly used for application to the skin or other body surface, and include ionizable inorganic salts, organic compounds, or combinations of both.

Examples of ionically conductive electrolytes include, but are not limited to, ammonium sulfate, ammonium acetate, monoethanolamine acetate, diethanolamine acetate, sodium lactate, sodium citrate, magnesium acetate, magnesium sulfate, sodium acetate, calcium chloride, magnesium chloride, calcium sulfate, lithium chloride, lithium perchlorate, sodium citrate and potassium chloride, and redox couples such as a mixture of ferric and ferrous salts such as sulfates and gluconates. Preferred salts are potassium chloride, sodium chloride, magnesium sulfate, and magnesium acetate, and potassium chloride is most preferred for EKG applications. Although virtually any amount of electrolyte may be present in the adhesive compositions of the invention, it is preferable that any water-soluble electrolyte be present at a concentration in the range of about 0.1 to about 15 wt % of the mixture. The procedure described in U.S. Pat. No. 5,846,558 to Nielsen et al. for fabricating biomedical electrodes may be adapted for use with the adhesive compositions of the invention, and the disclosure of that patent is incorporated by reference with respect to manufacturing details. Other suitable fabrication procedures may be used as well, as will be appreciated by those skilled in the art.

For certain applications, particularly when high cohesive strength is desired, the adhesive composition should be covalently crosslinked. The hydrophilic polymer may be covalently crosslinked, either intramolecularly or intermolecularly, and/or the hydrophilic polymer and the plasticizer may be covalently crosslinked. In the former case, there are no covalent bonds linking the hydrophilic polymer to the plasticizer, while in the latter case, there are covalent crosslinks binding the hydrophilic polymer to the plasticizer. The hydrophilic polymer, or the hydrophilic polymer and the plasticizer, may be covalently crosslinked using heat, radiation, or a chemical curing (crosslinking) agent.

For thermal crosslinking of the adhesive composition, a free radical polymerization initiator should be added into the polymer blend, i.e., the admixture of the hydrophilic polymer and the plasticizer. The free radical polymerization initiator can be any of the known free radical-generating initiators conventionally used in vinyl polymerization and is preferably an organic peroxide or azo compound. The initiators can be used in conventional amounts, generally from 0.01 to 15%, preferably 0.05 to 10%, more preferably from about 0.1% to about 5% and especially from a out 0.5% to about 4% by weight of the polymerisable material. Suitable organic peroxides include dialkyl peroxides such as t-butyl peroxide and 2,2 bis(t-butylperoxy)propane, diacyl peroxides such as benzoyl peroxide and acetyl peroxide, peresters such as t-butyl perbenzoate and t-butyl per-2-ethylhexanoate, perdicarbonates such as dicetyl peroxy dicarbonate and dicyclohexyl peroxy dicarbonate, ketone peroxides such as cyclohexanone peroxide and methylethylketone peroxide, and hydroperoxides such as cumene hydroperoxide and tert.butyl hydroperoxide. Suitable azo compounds include azo bis (isobutyronitrile) and azo bis (2,4-dimethylvaleronitrile). The temperature and thermally crosslink the adhesive composition will depend on the actual components and may be readily deduced by one of ordinary skill in the art, but typically ranges from about 80° C. to about 200° C.

The hydrophilic polymer, or the hydrophilic polymer and the plasticizer, may also be crosslinked with radiation, typically in the presence of a photoinitator. The radiation may be ultraviolet, alpha, beta, gamma, electron beam, and x-ray radiation, although ultraviolet radiation is preferred. Useful photosensitizers are triplet sensitizers of the "hydrogen abstraction" type, and include benzophenone and substituted benzophenone and acetophenones such as benzyl dimethyl ketal, 4-acryloxybenzophenone (ABP), 1-hydroxy-cyclohexyl phenyl ketone, 2,2-diethoxyacetophenone and 2,2-dimethoxy-2-phenylacetophenone, substituted alpha-ketols such as 2-methyl-2-hydroxypropiophenone, benzoin ethers such as benzoin methyl ether and benzoin isopropyl ether, substituted benzoin ethers such as anisoin methyl ether, aromatic sulfonyl chlorides such as 2-naphthalene sulfonyl chloride, photoactive oximes such as 1-phenyl-1,2-propanedione-2-(O-ethoxy-carbonyl)-oxime, thioxanthones including alkyl- and halogen-substituted thioxanthonse such as 2-isopropylthioxanthone, 2-chlorothioxanthone, 2,4 dimethyl thioxanone, 2,4 dichlorothioxanone, and 2,4-diethyl thioxanone, and acyl phosphine oxides. Radiation having a wavelength of 200 to 800 nm, preferably, 200 to 500 nm, is preferred for use herein, and low intensity ultraviolet light is sufficient to induce crosslinking in most cases. However, with photosensitizers of the hydrogen abstraction type, higher intensity UV exposure may be necessary to achieve sufficient crosslinking. Such exposure can be provided by a mercury lamp processor such as those available from PPG, Fusion, Xenon, and others. Crosslinking may also be induced by irradiating with gamma radiation or an electron beam. Appropriate irradiation parameters, i.e., the type and dose of radiation used to effect crosslinking, will be apparent to those skilled in the art.

Suitable chemical curing agents, also referred to as chemical cross-linking "promoters," include, without limitation, polymercaptans such as 2,2-dimercapto diethylether, dipentaerythritol hexa(3-mercaptopropionate), ethylene bis(3-mercaptoacetate), pentaerythritol tetra(3-mercaptopropionate), pentaerythritol tetrathioglycolate, polyethylene glycol dimercaptoacetate, polyethylene glycol di(3-mercaptopropionate), trimethylolethane tri(3-mercaptopropionate), trimethylolethane trithioglycolate, trimethylolpropane tri(3-mercaptopropionate), trimethylolpropane trithioglycolate, dithioethane, di- or trithiopropane and 1,6-hexane dithiol. The crosslinking promoter is added to the uncrosslinked hydrophilic polymer to promote covalent crosslinking thereof, or to a blend of the uncrosslinked hydrophilic polymer and the plasticizer, to provide crosslinking between the two components.

The hydrophilic polymer may also be crosslinked prior to admixture with the plasticizer. In such a case, it may be preferred to synthesize the polymer in crosslinked form, by admixing a monomeric precursor to the polymer with multifunctional comonomer and copolymerizing. Examples of monomeric precursors and corresponding polymeric products are as follows: N-vinyl amide precursors for a poly(N-vinyl amide) product; N-alkylacrylamides for a poly(N-alkylacrylamide) product; acrylic acid for a polyacrylic acid product; methacrylic acid for a polymethacrylic acid product; acrylonitrile for a poly(acrylonitrile) product; and N-vinyl pyrrolidone (NVP) for a polyviny lpyrrolidone product. Polymerization may be carried out in bulk, in suspension, in solution, or in an emulsion. Solution polymerization is preferred, and polar organic solvents such as ethyl acetate and lower alkanols (e.g., ethanol, isopropyl alcohol, etc.) are particularly preferred. For preparation of hydrophilic vinyl polymers, synthesis will typically take place via a free radical polymerization process in the presence of a free radical initiator as described above. The multifunctional comonomer include, for example, bisacrylamide, acrylic or methacrylic esters of diols such as butanediol and hexanediol (1,6-hexane diol diacrylate is preferred), other acrylates such as pentaerythritol tetraacrylate, and 1,2-ethylene glycol diacrylate, and 1,12-dodecanediol diacrylate. Other useful multifunctional crosslinking monomers include oligomeric and polymeric multifunctional (meth)acrylates, e.g., poly(ethylene oxide) diacrylate or poly(ethylene oxide) dimethacrylate; polyvinylic crosslinking agents such as substituted and unsubstituted divinylbenzene; and difunctional urethane acrylates such as EBECRYL® 270 and EBECRYL® 230 (1500 weight average molecular weight and 5000 weight average molecular weight acrylated urethanes, respectively—both available from UCB of Smyrna, Ga.), and combinations thereof. If a chemical crosslinking agent is employed, the amount used will preferably be such that the weight ratio of crosslinking agent to hydrophilic polymer is in the range of about 1:100 to 1:5. To achieve a higher crosslink density, if desired, chemical crosslinking is combined with radiation curing.

The adhesive compositions of the invention are extrudable, and thus may be prepared using a simple blending and extruding process. The components of the composition are weighed out and then admixed, for example using a Baker Perkins Blender, generally although not necessarily at an elevated temperature, e.g., about 35° C. to about 90° C. Solvents may, if desired, be added. Preferred solvents are aqueous solvents or alcohols (e.g., ethanol, methanol, isopropanol, etc.). Any crosslinking is carried out subsequently. The resulting composition can be extruded using a single or twin extruder, or pelletized.

In the manufacture of transdermal (or transmucosal) drug delivery system, the adhesive composition may be prepared or extruded onto the backing layer or release liner of such a system. That is, such drug delivery systems generally comprise: (A) a drug reservoir containing a therapeutically effective amount of the active agent; (B) an adhesive means for maintaining the system in active agent transmitting relationship to a body surface; and (C) a backing layer that serves as the outer surface of the device during use, wherein (D) a release liner generally covers the exposed adhesive during storage and prior to use.

Any number of active agents can be administered using the drug delivery systems of the invention. Suitable active agents include the broad classes of compounds normally delivered through body surfaces and membranes; these active agents, in general, include: analeptic agents; analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder ("ADD") and attention deficit hyperactivity disorder ("ADHD") drugs; cardiovascular preparations including calcium channel blockers, antianginal agents, central nervous system ("CNS") agents, beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; peptide drugs; psychostimulants; sedatives; steroids, including progestogens, estrogens, corticosteroids, androgens and anabolic agents; smoking cessation agents; sympathomimetics; tranquilizers; and vasodilators including general coronary, peripheral and cerebral. Specific active agents with which the present adhesive compositions are useful include, without limitation, anabasine, capsaicin, isosorbide dinitrate, aminostigmine, glyceryl trinitrate, verapamil, propranolol, silabolin, foridone, clonidine, cytisine, phenazepam, nifedipine, fluacizin, and salbutamol.

With some active agents, it may be necessary to administer the drug along with a permeation enhancer in order to achieve a therapeutically effective flux through the skin. Suitable enhancers include, for example, the following: sulfoxides such as dimethylsulfoxide (DMSO) and decylmethylsulfoxide ($C_{10}$MSO); ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclazacycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate ("PEGML"; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid. Mixtures of two or more enhancers may also be used. A preferred enhancer is ethanol, which not only serves as a permeation enhancer, but also solubilizes many active agents of interest and in addition improves adhesion. An ethanol-water mixture may also be used. It is pertinent to note, that a range of above mentioned skin permeability enhancers serves concomitantly in the adhesive composition as appropriate plasticizing agents, e.g. polyols such as propylene glycol, ethylene glycol, glycerol, butanediol, hexanediol and polyethylene glycol.

The backing layer of the transdermal drug delivery device functions as the primary structural element of the transdermal system and provides the device with flexibility, drape and, optionally, occlusivity. The material used for the backing layer should be inert and incapable of absorbing drug, enhancer or other components of the pharmaceutical composition contained within the device. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides. The layer is preferably in the range of about 15 microns to about 250 microns in thickness, and may, if desired, be pigmented, metallized, or provided with a matte finish suitable for writing. The layer is preferably nonocclusive (or "breathable"), i.e., is preferably permeable to moisture.

During storage and prior to use, the laminated structure includes a release liner. Immediately prior to use, this layer is removed from the device so that the system may be affixed to the skin. The release liner should be made from a drug/vehicle impermeable material, and is a disposable element which serves only to protect the device prior to application. Typically, the release liner is formed from a material impermeable to the components of the device and the pharmaceutical composition contained therein.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be a drug, a permeation enhancer, or some other component contained in the drug delivery system.

In any of these transdermal systems, it may be desirable to include a rate-controlling membrane in the system on the skin side of the drug reservoir. The materials used to form such a membrane are selected to limit the flux of one or more components contained in the drug formulation, and the membrane may be either microporous or dense. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, polysiloxane-polycarbonate block copolymer and the like.

The adhesive compositions of the invention are useful in any number of additional contexts wherein adhesion of a product to a body surface is called for or desirable. These applications include, for example, pressure-relieving cushions for application to a foot, wherein the cushions may or may not contain medication for transdermal or topical delivery, e.g., salicylic acid or the like. Such cushions will generally be comprised of a flexible, resilient outer layer, fabricated from a foam pad, fabric, or the like, with a layer of an adhesive composition of the invention laminated thereto for application to the skin surface. In this embodiment, cohesive strength is important for the product to function as a pressure-relieving cushion, and the hydrophilic polymer should therefore be covalently crosslinked to a degree sufficient to impart the necessary cohesive strength.

Another application of the present adhesives is in wound dressing products and other medical skin coverings such as adhesive tapes or the like. Such adhesive compositions may or may not be medicated; if medicated, they will generally contain anti-infective agents and/or other types of pharmacologically active agents. Medical skin coverings such as adhesive tapes and wound dressings may be readily fabricated using conventional manufacturing techniques, including the procedure described in U.S. Pat. No. 5,985,990, the disclosure of which is incorporated by reference herein.

The adhesive compositions are also useful in conjunction with medical devices to be affixed to a body surface, diagnostic systems or devices to be affixed to a body surface, and any other application wherein adhesion to a body surface is necessary or desired.

Accordingly, the present invention represents an important advance in the field of pressure sensitive adhesives, particularly bioadhesives. The novel adhesive compositions adhere well to hydrated surfaces such as mucosal tissue, are suitable for long-term skin contact and are nonirritating, noncomedogenic and nonsensitizing, are permeable to and physically and chemically compatible with a variety of drugs and drug types, and can enhance the rate at which an active agent migrates into a body surface. Furthermore, the present adhesive composition can be used in a variety of contexts, and can be readily tailored during manufacture with respect to hygroscopicity and the desired degree of hydrophilicity, adhesive and cohesive strength.

The practice of the present invention will employ, unless otherwise indicated, conventional techniques of drug delivery and associated manufacturing techniques, which are within the skill of the art. Such techniques are fully explained in the literature. See Remington: The Science and Practice of Pharmacy, cited supra, as well as Goodman & Gilman's The Pharmacological Basis of Therapeutics, 9th Ed. (New York: McGraw-Hill, 1996).

It is to be understood that while the invention has been described in conjunction with the preferred specific embodiments thereof, the foregoing description, as well as the examples which follow, are intended to illustrate and not limit the scope of the invention. Other aspects, advantages and modifications will be apparent to those skilled in the art to which the invention pertains. All patents, patent applications, journal articles and other references cited herein are incorporated by reference in their entireties.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLES 1-16

Preparation of PSA Matrices by Blending PVP and PEG400: Effects of Composition, Hydration and the Thickness of Adhesive Layer Adhesive films of 250-300 μm in thickness were prepared by dissolving hydrophilic polymers and PEG ($M_w$=400) in a common solvent (ethyl alcohol) followed by casting the solution on a backing film and drying. Unsupported PVP-PEG hydrogels were obtained by casting the relevant solutions onto release liner followed by drying at ambient temperature.

Adhesive joint strength of the adhesive hydrogels to standard polyethylene (PE) film of 100 m in thickness was evaluated by a 180° peel test with an Instron 1221 Tensile Strength Tester at the peeling rate of 10 mm/min. A low-density PE film, crystallinity 45%, contact angle 105°, surface energy 28.5 mJ/m$^2$, was employed as a standard substrate. The adhesives were saturated with water by equilibrating in dessicators with a controlled pressure of water vapor of 50% at ambient temperature for 6-7 days. The time to attain a maximum strength of adhesive contact with the substrate was 15-20 min. The character of adhesive joint failure was observed with a TV camera interfaced to an IBM computer and photographed with a microscope. The locus of failure was ascertained by contact angle measurement of the detached substrate surface.

Phase behavior of the hydrophilic polymers blends with PEG-400 over an entire compositional range was investigated by Differential Scanning Calorimetry (DSC) using a Mettler TA 4000/DSC-30 differential scanning calorimeter calibrated with indium and gallium. In the DSC apparatus, the samples were first quench cooled with liquid nitrogen from ambient temperature to −100° C. over 2-3 minutes and then heated at a rate of 20° C. min$^{-1}$ to 220° C. Upon heating, a heat capacity jump followed by a single exotherm coupled with a symmetric endotherm, and a high temperature endotherm, were normally observed for the blends. These four transitions were respectively attributed to glass transition, PEG cold crystallization, melting, and water thermodesorption (see Feldstein et al. (2000), "Coherence of thermal transitions in poly(N-vinyl pyrrolidone)-poly (ethylene glycol) compatible blends," Polymer 41(14) :5327-5359). The glass transition temperatures, $T_g$, were recorded at half-height of the relevant heat capacity jumps in DSC heating thermograms. All reported values are the average of replicate experiments varying less than 1-2%. Samples of 5-15 mg in weight were sealed in standard aluminum pans supplied with pierced lids so that absorbed moisture could evaporate upon heating. An argon purge (50 mL $min^{-1}$) was used to avoid moisture condensation at the sensor. The content of absorbed water in the blends was determined by weighing the samples before and after DSC scans using a Mettler Analytical Balance, AE 240, with an accuracy of ±0.01 mg. Weight loss of the sample after scanning was compared to the amount of desorbed water evaluated from the enthalpy change associated with water evaporation from the sample by DSC.

Water vapor sorption: Adhesive films were equilibrated at room temperature in desiccators over aqueous $H_2SO_4$ solutions of controlled density which maintained the required relative humidity ranged from 10 to 90%. Equilibrium water sorption was measured gravimetrically and confirmed with a vacuum assembly containing a quartz-spring microbalance.

Viscoelastic properties and the durability of adhesive joints of adhesive hydrogels were studied using a squeeze-recoil technique on a DTDM thermomechanical analyzer (microdilatometer) as described by Kotomin et al. (1999), "Squeeze-recoil analysis of adhesive hydrogels and elastomers" Polym Mater. Sci. Eng. 81:425-426 and Kotomin et al. (2000), "Durability and fracture of some viscoelastic adhesives" Proceed. 23$^{rd}$ Adhesion Soc. Annual Meeting, Myrtle Beach, S.C., pp. 413-415. The polymer sample was placed between two flat silica surfaces formed by loading rod and supporting plate and subjected to the action of a fixed compressive load, followed by removing the compressive load to allow the sample relaxation.

Table 2 reports the properties of PVP adhesive blends with PEG-400. Examples 1-4 and FIGS. 2 and 3 demonstrate the effect of PVP-PEG blend composition on adhesive properties. The relationship of adhesion to the phase behavior of PVP-PEG blends is also shown, described in terms of the negative $T_g$ deviation from the weight-average magnitudes ($-\Delta T_g$), found with the Fox equation (1), and the $\Delta C_p T_g$ value. In the PVP-PEG blends, the adhesion appears in a narrow range of concentration. The maximum adhesion corresponds to the maximum $-\Delta T_g$ values and to the minimum $\Delta C_p T_g$ value. While not wishing to be bound by theory, the implication of the former finding would appear to be that the adhesion is provided by the formation of a stoichiometric hydrogen-bonded network PVP-PEG complex. This conclusion can be established by a comparison of the compositional profile of adhesion with the data on PVP-PEG hydrogen bonding presented in Feldstein et al. (2001), "Relation of glass transition temperature to the hydrogen bonding degree and energy in poly(N-vinyl pyrrolidone) blends with hydroxyl-containing plasticizers: 2. Effects of poly (ethylene-glycol) chain length," Polymer 42:981-990. The latter observation implies that the adhesion is controlled by a specific counterbalance of enhanced free volume against the strong favorable interaction between blended components: high molecular weight PVP and short-chain PEG macromolecules, bearing reactive groups at both chain ends (Feldstein et al. (1999), "Contribution of molecular mobility to debonding of pressure-sensitive adhesive hydrogels," Polym Mater. Sci. Eng. 81:467-468).

Figure 9:
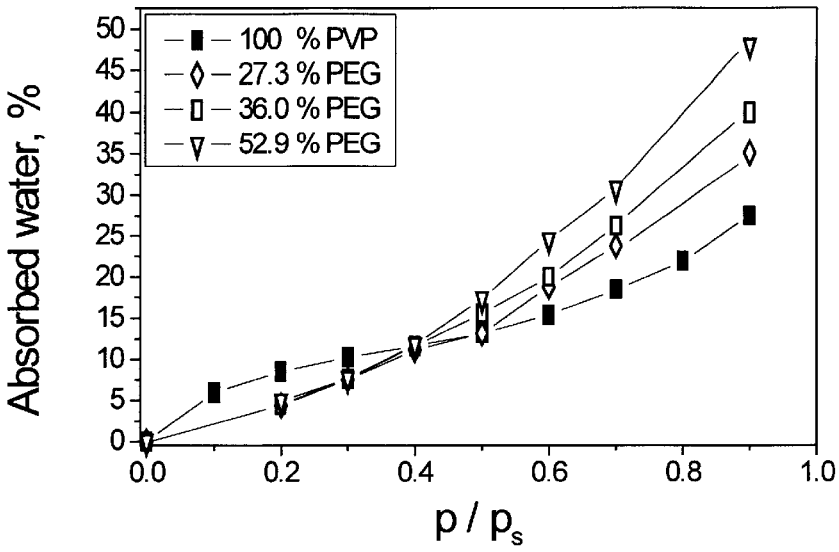
FIG. 9 exhibits the water vapor absorption isotherms for PVP and its blends with PEG-400 at ambient temperature.

Examples 1, 5-9 and FIG. 4 reveal the impact of relative humidity (RH) of the surrounding atmosphere on the adhesive behavior of PVP-PEG blends. PVP is a hygroscopic polymer that absorbs more than 25% water upon exposure to a high RH (FIG. 9). With PVP-overloaded blends, having higher glass transition temperatures, where debonding proceeds through an adhesive mechanism, the blend hydration increased the force required to rupture adhesive bond. In contrast, with PEG-overloaded, plasticized blends, the effect of additional plasticizer reduces the adhesion. As a result of enhanced fluidity and decreased cohesive strength of the hydrophilic composite, an adhesive remainder occurs at the substrate interface upon adhesive joint failure (Table 1).

Examples 1, 10 and 11 exhibit the effects of the chain length of the hydrophilic polymer (PVP) on adhesive joint strength. In general, peel strength of an adhesive joint tended to decrease with the reduction of molecular weight. Examples 12-16 demonstrate the impact of adhesive layer thickness upon adhesive joint strength. In accordance with Equation 2, the peel force required to rupture an adhesive joints was found to increase with the increase in thickness of the adhesive layer.

TABLE 2

Adhesive properties and phase behavior of PVP blends with PEG-400/

| No. | PVP MW | Composition, wt % PVP | PEG-400 | RH, % | Thickness (μm) | $\Delta T_g$, K | $\Delta C_p T_g$, J/g | Peel Force, N/m | Debonding mode |
|---|---|---|---|---|---|---|---|---|---|
| 1. | 1,000,000 | 64 | 36 | 50 | 130 | 71 | 46.2 | 370 | misc. |
| 2. | | 73 | 27 | | | 39 | 119.0 | 83 | adhesive |
| 3. | | 54 | 46 | | | 65.2 | 92.6 | 95 | cohesive |
| 4. | | 47 | 53 | | | 37.2 | 77.2 | 64 | cohesive |
| 5. | | 64 | 36 | 20 | 130 | 69 | | 30 | adhesive |
| 6. | | | | 40 | | 73 | | 90 | adhesive |
| 7. | | | | 65 | | 70.5 | 59.1 | 330 | cohesive |
| 8. | | | | 80 | | 66.2 | | 42 | cohesive |
| 9. | | | | 90 | | 77 | 96.0 | — | cohesive |
| 10. | 150,000 | 64 | 36 | 50 | 130 | | 82.0 | 15 | cohesive |
| 11. | 8,000 | | | | | | 87.5 | 0 | cohesive |
| 12. | 1,000,000 | 64 | 36 | 50 | 250 | | | 390 | misc. |
| 13. | | | | | 175 | | | 390 | misc. |
| 14. | | | | | 119 | | | 330 | adhesive |
| 15. | | | | | 70 | | | 210 | adhesive |
| 16. | | | | | 50 | | | 185 | adhesive |

EXAMPLES 17-47

Preparation of PSA Matrices by Blending PVP with Different Short-chain Plasticizers. Effects of Composition, and the Relation of Adhesion to Phase State Using the preparation procedure and evaluation tests described in Example 1, the samples of PVP K-90 blends with various plasticizers were obtained and tested at 50% RH and ambient temperature. The results are set forth in the Table 3. The tacky blends can be obtained by mixing PVP with hydroxyl-terminated (Examples 17-41) or carboxyl terminated (Examples 42-47) short-chain plasticizers. Short-chain plasticizers include: ethylene glycol (Examples 17-19) and its polymers (PEG), ranging in molecular weight from 200 to 600 g/mol (Examples 20-23); low molecular weight 1,3- and 1,2-propylene glycol (PG) (Examples 24, 25); and alkane diols from propane diol up to pentane diols (PD) and hexane diol (HD) inclusive (Examples 27-39). Polypropylene glycol (PPG) has been found to be a good plasticizer for PVP, but does not develop any adhesion or tack (Example 26). The glass transition temperatures of plasticizers examined were within the range of −59° C. to −116° C. To induce adhesion, the plasticizer has to be either amorphous or crystalline, but the melting temperature of appropriate plasticizers, $T_m$, is normally lower than 50° C., the value found for 1,6-hexane diol (HD) (Examples 33-37). The adhesive strength correlates with maximum $-\Delta T_g$ and minimum $\Delta C_p T_g$ values. The highest peel strength was found for PVP blends with glycerol (Example 41), which possesses a high density of hydroxyl groups per molecule. Strictly speaking, the carbonic diacids of Table 3 and Examples 44-47 are not acting as plasticizers but rather as noncovalent crosslinking agents and cohesive interaction enhancers. For proper adhesion, carbonic diacids can be employed in combination with plasticizers so as to reduce $T_g$ to the values inherent in PSAs. Such approach has been used in a Plastoid adhesive blend (U.S. Pat. Nos. 5,730,999 and 5,993,849, EP 848960 A3), where EUDRAGIT E-100 was crosslinked by succinic acid and plasticized with tributylcitrate. Dry blends of PVP with 50% of carbonic diacids have been found to exhibit high $T_g$ values (28,-34,-43, and 24° C. for SA, MA, GA, and AA, respectively) and, therefore, develop no adhesion. However, once the blends are hydrated, their glass transition temperatures decrease to −55° C. to −65° C., and adhesion appears (see Examples 44-47). The PEG-600, terminated by carboxyl groups (Examples 42, 43), serves as both a crosslinking agent and a plasticizer, imparting adhesion to PVP blends.

EXAMPLES 48-64

PSA Compositions Prepared by Mixing Different Hydrophilic Polymers with Complementary Short-chain Plasticizers These examples demonstrate that not only PVP but a range of different hydrophilic polymers become tacky upon mixture with short-chain plasticizers bearing complementary reactive groups at the chain ends. Suitable hydrophilic polymers include poly(N-vinyl amides) such as PVP (Examples 1-47), poly(N-vinyl caprolactam) (PVCap) (Examples 48-52) and poly(N-vinyl acetamide) (PVAA, Example 53), poly(N-alkyl acrylamides), exemplified by poly(N-isopropyl acrylamide) (PNIPAM, Example 54), polymethacrylic and polyacrylic acid (PMA, PAA, Examples 55-60), and the copolymers thereof exemplified in the Table 4 (Luviscols VAP®, commercially available from BASF; Examples 61-64). Luviscol VAP 37 is a copolymer of vinylpyrrolidone (VP, 30%) with 70% vinylacetate (VA). Luviscol VAP 73 contains 70% of VP and 30% of VA.

Figure 10:
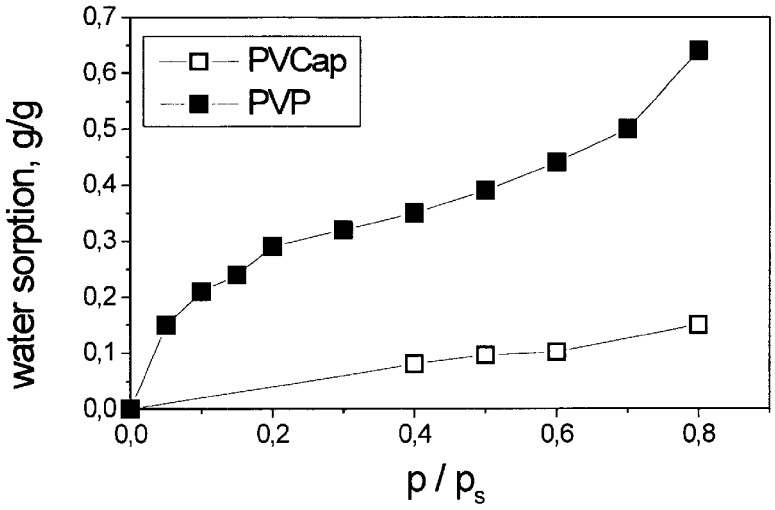
FIG. 10 displays the isotherms of water vapor sorption by polyvinyl caprolactam (PVCap) and PVP at ambient temperature.
Figure 11:
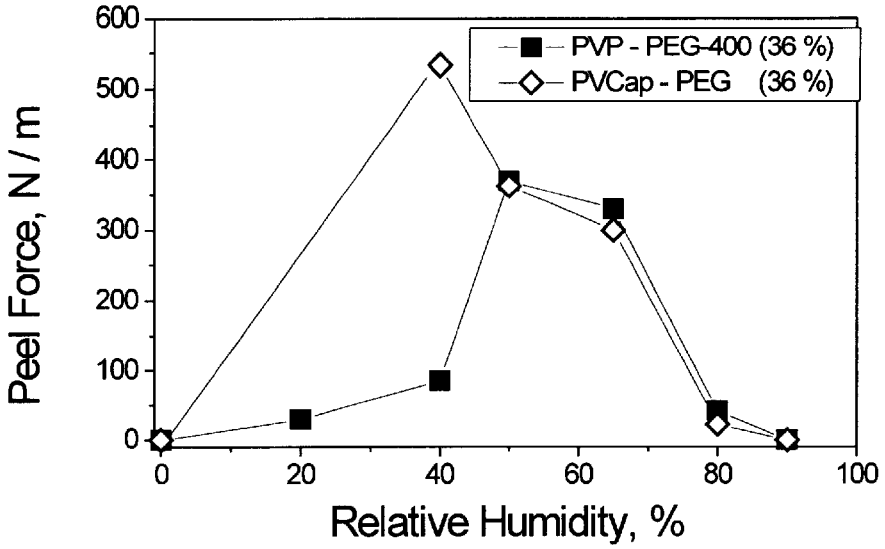
FIG. 11 outlines the effect of relative humidity (RH) on the adhesion of PVP-PEG and PVCap-PEG hydrogels.

Among the polymers in Table 4, the best performance properties were found for PEG-400 blends with PVCap. The data presented in FIGS. 9-11 compare the hygroscopicity and adhesion of PVPCap-PEG-400 and PVP-PEG-400 blends. As follows from the data in FIG. 10, the PVPCap takes up nearly four times less water than PVP under comparable conditions. According to the Zaikov-Iordanskii-Markin classification of polymer hydrophilicity, PVP is hygroscopic, whereas PVCap is a moderately hydrophilic polymer. Compared to a PVP blend with 36 wt. % of PEG-400, the PVCap plasticized with the same amount of PEG-400 exhibited much higher adhesion. The left branches of the curves in FIG. 11 correspond to adhesive debonding, while the right branches correspond to miscellaneous and cohesive types of adhesive bond failure. As follows from Examples 1, 10, and 11, increase in polymer molecular weight results in an increase in cohesive toughness and adhesion. The sorption and adhesive properties of PVCap-PEG hydrogels are thus ideal for pharmaceutical applications. It should also be noted that PVCap exhibits a Lower Critical Solution Temperature (LCST) about 35° C. (see Kirsh Y E., Water soluble poly(N-vinylamides), Wiley, N.Y., 1998). Below this temperature the PVCap is easily soluble in water and behaves like moderately hydrophilic polymer, while above LCST the PVCap becomes insoluble in water hydrophobic polymer. This property is highly useful for the development of thermoresponsive or so-called "smart" adhesive hydrogels.

TABLE 3

Adhesive and phase properties of PVP blends with short-chain plasticizers

| | | | | Composition, wt. % | | | $\Delta C_p T_g$, | Peel Force, Debonding | |
|---|---|---|---|---|---|---|---|---|---|
| No. | Plasticizer | $T_g$, ° C. | $T_m$, ° C. | Plasticizer | PVP | $-\Delta T_g$, K | J/g | N/m | mode |
| 17. | Ethylene glycol | −112 | | 25 | 75 | n/d | n/d | 123 | adhesive |
| 18. | | | | 36 | 64 | 60 | 62.0 | 142 | adhesive |
| 19. | | | | 45 | 55 | n/d | n/d | 127 ± 15 | adhesive |
| 20. | PEG-200 | −70 | n/a | 36 | 64 | 82 | | 195 | cohesive |
| 21. | PEG-300 | −70 | n/a | | | 75 | | 110 | adhesive |
| 22. | PEG-600 | −70 | 16 | | | 68 | 75.3 | 15 | adhesive |
| 23. | PEG-1000 | −70 | 39 | | | 60 | 22.7[1] | 0 | — |
| 24. | 1,3-Propylene Glycol | −116 | n/a | 35 | 65 | 55 | 47.9 | 116 ± 10 | adhesive |
| 25. | 1,2-Propylene Glycol | −95 | n/a | 35 | 65 | 42 | 56.5 | 180 ± 20 | adhesive |
| 26. | PPG-425 | −68 | n/a | 34 | 66 | 75 | 68.3 | 0 | — |

TABLE 3-continued

Adhesive and phase properties of PVP blends with short-chain plasticizers

| No. | Plasticizer | $T_g$, ° C. | $T_m$, ° C. | Composition, wt. % Plasticizer | PVP | $-\Delta T_g$, K | $\Delta C_p T_g$, J/g | Peel Force, N/m | Debonding mode |
|---|---|---|---|---|---|---|---|---|---|
| 27. | 1,5-PD | −104 | −12.5 | 43 | 57 | 0 | 47.1 | 0 | — |
| 28. | | | | 50 | 50 | 55 | 72.6 | 30 | cohesive |
| 29. | | | | 66.5 | 33.5 | 32.5 | 105.0 | 10 | cohesive |
| 30. | 2,4-PD | −59 | n/a | 32 | 68 | 02 | 59.7 | 0 | adhesive |
| 31. | | | | 49 | 51 | 65.4 | 89.0 | 190 | adhesive |
| 32. | | | | 65.5 | 34.5 | 39.5 | 140.1 | 0 | cohesive |
| 33. | 1,6-HD | −99 | 49.1 | 33 | 67 | 27.4 | 29.3[2] | 0 | — |
| 34. | | | | 37.6 | 62.4 | 83.1 | 59.6 | 11 | cohesive |
| 35 | | | | 45 | 55 | | | 64.6 | cohesive |
| 36. | | | | 50 | 50 | 55.6 | 58.6 | 19 | cohesive |
| 37. | | | | 66.6 | 33.4 | 38.5 | 101.0 | 0 | cohesive |
| 38. | 2,5-HD | −62 | n/a | 49 | 51 | 65.3[2] | 76.4 | 26 | adhesive |
| 39. | | | | 66 | 34 | 40.1 | 122.2 | 10 | cohesive |
| 40. | Glycerol | −74 | n/a | 23.4 | 76.6 | 138.1 | 45.9[2] | — | adhesive |
| 41. | | | | 38 | 62 | 70.5 | 85.7 | 850 | misc. |
| 42. | Carboxyl-terminated | −49 | 12 | 36 | 64 | 75[2] | 55.9 | 8.5 | adhesive |
| 43. | PEG-600 | | | 50 | 50 | 55 | 112 | 346.5 ± 15 | cohesive |
| 44. | Succinic acid (SA) | n/d | 188 | 50 | 50 | n/d | 26.1/75.0[3] | 0/62 | adhesive |
| 45. | Malonic acid (MA) | n/d | 135 | 50 | 50 | n/d | 52.5/80.1[3] | 7.6/71 | adhesive |
| 46. | Glutaric acid (GA) | n/d | 96 | 50 | 50 | n/d | 129/85[3] | 0/94 | adhesive |
| 47. | Adipic acid (AA) | n/d | 152 | TBD | TBD | n/d | 58.1/89[3] | TBD | adhesive |

[1]The $\Delta C_p$ value has been found to be decreased due to a high degree of blend crystallinity.
[2]The blend is inhomogeneous. Two glass transitions are observed. The data relate to the lower glass transition temperature.
[3]The data refer to dry blends and those containing 25% of water, respectively.

TABLE 4

Adhesive properties of PEG-400 miscible blends with various hydrophilic polymers.

| No. | Polymer/ Plasticizer | Polymer MW | $T_g$, ° C. | Composition, wt. % Polymer | Plasticizer | RH, % | $-\Delta T_g$, K | $\Delta C_p T_g$, J/g | Peel Force N/m | Debond. mode |
|---|---|---|---|---|---|---|---|---|---|---|
| 48. | PVCap/PEG-400 | 100,000 | 165 | 64 | 36 | 40 | 71 | 88.3 | 533 | misc. |
| 49. | | | | | | 50 | | | 363 | cohesive |
| 50. | | | | | | 60 | | | 300 | cohesive |
| 51. | | | | | | 80 | | | 23 | cohesive |
| 52. | PVCap/PEG400 | 1,000,000 | 197 | 64 | 36 | 50 | 81 | 98.0 | 150 | adhesive |
| 53. | PVAA/PEG400 | 1,000,000 | | 64 | 36 | 50 | | | 397 | adhesive |
| 54. | PNIPAM/PEG400 | 250,000 | 157 | 64 | 36 | 50 | 66 | 89.0 | 230 | misc. |
| 55. | PMAA*/PEG400 | 150,000 | | 36 | 64 | 50 | — | — | 0 | — |
| 56. | | | | 47 | 53 | | — | — | 27.5 ± 5 | adhesive |
| 57. | | | | 63 | 37 | | — | — | 72 | cohesive |
| 58. | PAA/PEG400 | 150,000 | | 47 | 53 | 50 | | | 51 | adhesive |
| 59. | PMAA*/1,5 PD | 150,000 | | 36 | 64 | 50 | — | — | 0 | — |
| 60. | | | | 50 | 50 | | — | — | 22.3 | adhesive |
| 61. | Luvisco173/PEG400 | 100,000 | 57.5 | 30 | 70 | 50 | 37.1 | 65.9 | High** | cohesive |
| 62. | | | | 36 | 64 | | 34.0 | 79.4 | High** | cohesive |
| 63. | Luvisco137/PEG400 | 100,000 | 29 | 17 | 83 | 50 | 9.3 | 138.7 | High** | cohesive |
| 64. | | | | 36 | 64 | | 24.4 | 180.1 | High** | cohesive |

*PMAA exhibits no glass transition; therefore, the negative deviation from weight-average magnitudes cannot be evaluated.
**Adhesion is very strong, but cannot be measured because the blend provides an inseparable adhesive joint with siliconized release liner.

Figure 6:
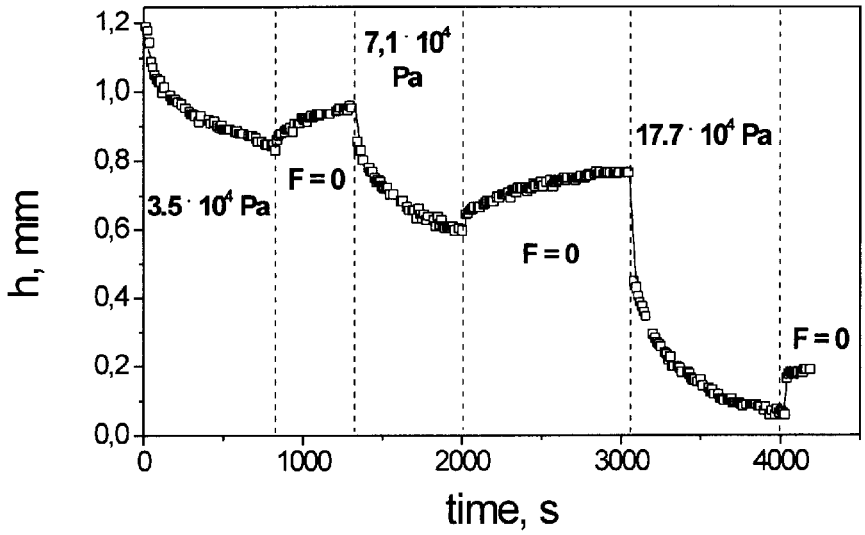
FIG. 6 illustrates the squeezing kinetics of PVP-PEG adhesive hydrogel under a fixed compressive load and squeeze recoil upon its removal. The h value is the distance (mm) between the upper and lower plates of the squeeze-recoil tester, which is equal to the thickness of specimen.
Figure 7:
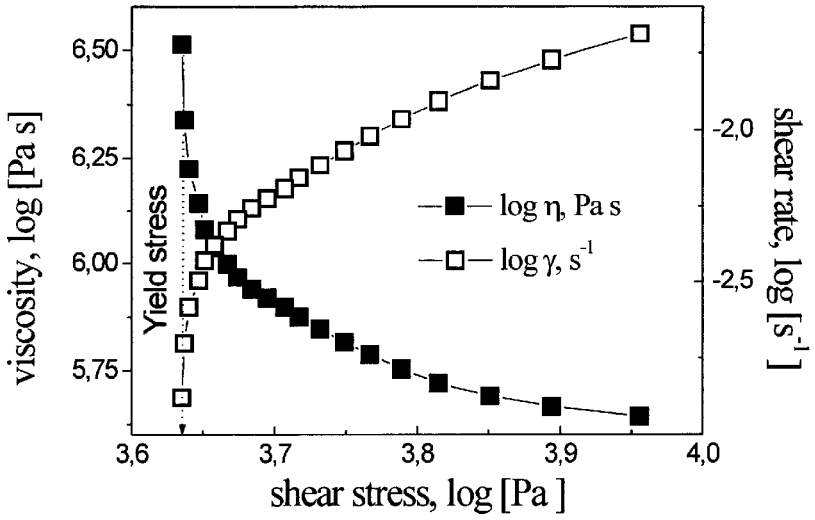
FIG. 7 is the PVP-PEG adhesive hydrogel flow curve under a compressive load of 1 N at 20° C.
Figure 8:
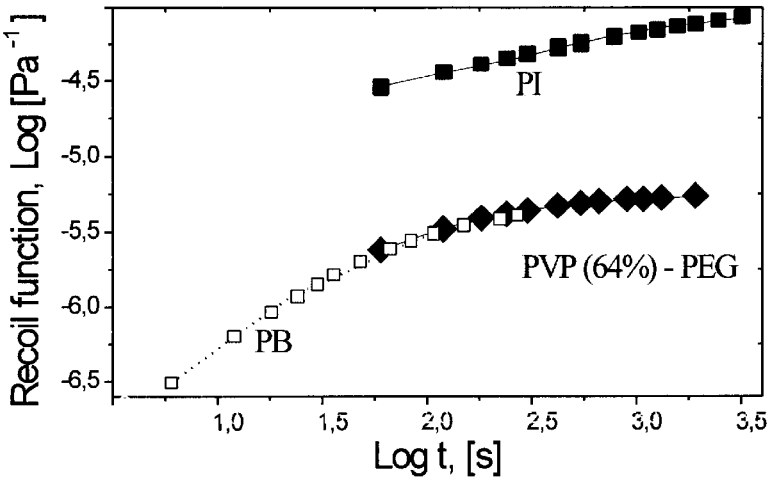
FIG. 8 outlines the creep-recoil functions for the PVP-PEG adhesive hydrogel compared to polybutadiene (PB) and polyisoprene (PI) rubbers.

In addition to pressure-sensitive adhesion, the adhesive hydrogels of the invention display a number of useful viscoelastic properties, similar to the properties of cured rubbers (FIGS. 6-8). In fact, adhesive hydrogels are hydrophilic and water-soluble rubbers, featuring rubber-like elasticity as one of their major performance properties. Both the rubber-like elastic and viscous contributions to the rheology of the present adhesive hydrogels are illustrated by the data in FIG. 6.

Under a fixed compressive force, hydrogel squeezing occurs, and the instantaneous compressibility (Hooke's elasticity) of the PVP-PEG adhesive hydrogel is proportional to the applied compressive load (FIG. 6). Hooke's compression is followed by a squeezing flow (creep), which reflects the viscous flow contribution to hydrogel rheology. As compression is developing, the stress within the adhesive polymer decreases gradually, achieving a critical value of yield stress at which the hydrogel ceases to flow and the squeezing flow is stopped. Occurrence of yield stress is a characteristic feature of crosslinked or highly ordered supramolecular structures, typical of polymer networks or liquid-crystalline polymers. Commodity polymers exhibit no yield stress. The yield stress in the PVP-PEG adhesive hydrogel is associated with a critical magnitude of shear stress in the flow curve shown in FIG. 7, at which the apparent shear viscosity climbs to infinity and the deformation rate drops tending to zero. The yield stress is an integral measure of cohesive strength, which has been shown to relate to the $\sigma_f$ value in equation (2) and which determines the adhesive properties of an adhesive polymer (Feldstein et al. (2000), "Molecular insight into theological and diffusion determinants of pressure-sensitive adhesion," Proceed. 23$^{rd}$ Annual Meeting Adhesion Soc., pp. 54-56).

Upon removal of compressive load, the relaxation of polymer deformation occurs, termed the "retardation," when deformation changes its sign and the polymer returns, more or less, to its initial shape. Again, the adhesive hydrogel demonstrated (FIG. 6) the instantaneous (Hooke's) retardation, followed by a creep recoil. The Hooke's elastic retardation value is proportional to compressive force (FIG. 6), and the slope of this linear relationship outlines the elastic relaxation shear modulus of adhesive hydrogel $G=2\cdot10^5$ Pa. This value found for the PVP-PEG adhesive hydrogel is well known to be also inherent in various PSA polymers and slightly crosslinked rubbers.

Upon the removal of compressive bonding force, the adhesive hydrogel is allowed to relax and creep recovery occurs, accompanied by a gradual growth in creep compliance, FIG. 8. Kinetics of PVP-PEG hydrogel creep recovery, described by creep-recoil function S(t), follow the phenomenological Dickie-Ferry equation (4), based on the model developed to describe the relaxation of slightly crosslinked rubbers:

$$S(t) = S_e\left[1 + \left(\frac{t}{\tau}\right)^{-n}\right]^{-1} \tag{4}$$

where S(t) is recoil compliance and $S_e$ is the equilibrium tensile compliance, t=time, $\tau$ is a characteristic (retardation) time, n denotes a Chasset-Thirion exponent. Computer simulation of the recoil function kinetic profiles in FIG. 8 provide the evaluation of PVP-PEG hydrogel equilibrium creep recoil compliance $S_e=1.56\cdot10^{-5}$ Pa$^{-1}$, retardation time $\tau=1.8\cdot10^3$ s and the Chasset-Thirion exponent n=0.99. The obtained Se magnitude corresponds to an average molecular weight of polymer chain between entanglements Mc≈130,000 g/mol, which is typical of slightly cross-linked rubbers, whereas the n value is a characteristic of highly dense network. Thus, the obtained $S_e$ and $\tau$ values refer most likely to the contribution of network formed by the entanglements of PVP chains, while the n exponent relates to the contribution of the much more dense and faster relaxing H-bonded network. The superposition of the recoil compliance profiles for PVP-PEG hydrogel and PB rubber (FIG. 8) provides evidence that the hydrogel retardation properties are typical of elastomers. Accordingly, the adhesive hydrogels described represent, in essence, water-soluble rubbers.

EXAMPLES 65-82

Therapeutic Systems Based on Hydrophilic PSA Matrices

Preparation:

Therapeutic agents (drugs) were first dissolved in a mixture of PEG-400 (plasticizer) and ethyl alcohol (solvent). Upon complete drug dissolution, the PVP or another hydrophilic polymer was dissolved in the earlier prepared mixture, forming casting solution that was cast onto polyethylene terephthalate backing film of 0.02 mm in thickness and dried at temperatures of 20-60° C.

In vitro drug delivery rate determination from water-soluble PSA matrices was performed using human cadaver skin or a skin-imitating Carbosil membrane to protect the matrices from dissolving in the receptor solution. The patch was adhered to the center of a Carbosil membrane sheet of twice its area. The membrane margins were then wrapped around the sample. The back side of the packet was closely attached to a steel plate-holder to prevent direct contact of the matrix with the receptor solution. In a similar fashion, cadaver skin epidermis can be used instead of a Carbosil membrane. The holder with the wrapped sample was then submerged into an aqueous sink and in vitro drug delivery rate was determined using a USP rotating cylinder method paddle-over-disc. The rate of drug appearance rate in a receptor solution (0.15 M NaCl) at 35.0±0.5° C. was determined spectrophotometrically.

Drug permeability coefficients through skin epidermis ($P_s$) and a Carbosil membrane ($P_m$)were measured as the fluxes of drug delivered from the hydrophilic PSA matrix normalized by the drug concentration in the donor vehicle, taking the matrix density (1.10±0.12 g/cm$^3$) into account.

Results

The compositions and properties of prepared therapeutic systems are presented in the Table 5.

TABLE 5

Properties of drug-loaded hydrophilic matrices.

| | Drug | Matrix composition | Drug content in the matrix (%) | Delivery rate in vitro μg/cm$^2$h across: Carbosil | Human skin | $P_m$ ($10^4$) cm/h | $P_s$ ($10^4$) cm/h |
|---|---|---|---|---|---|---|---|
| 65. | Anabasine | PVP-PEG | 1.6 | 150 ± 20 | | 106.3 ± 12.0 | |
| 66. | Isosorbide dinitrate | PVP-PEG | 9.6 | 384 ± 48 | 13.0 ± 4.3 | 44 ± 5 | 1.5 ± 0.5 |
| 67. | Isosorbide dinitrate | PVCap-PEG | 9.6 | 411 ± 49 | | 47.1 ± 5 | |
| 68. | Aminostigmine | PVP-PEG | 14.3 | 625 ± 20 | | 33.7 ± 12.0 | |
| | | | 7.6 | 263 ± 10 | | | |
| | | | 4.0 | 65 ± 5 | | | |
| 69. | Glyceryl trinitrate | PVP-PEG | 7.3 | 160 ± 40 | 12.4 ± 4.0 | 25.6 ± 1.4 | 1.9 ± 0.5 |
| | | | 1.9 | 45 ± 12 | | | |
| 70. | Verapamil | PVP-PEG | 39.1 | 110 ± 20 | | 21.4 ± 1.5 | 0.4 ± 0.1 |
| | | | 24.3 | 110 ± 16 | | | |
| | | | 13.8 | 95 ± 19 | 6 ± 2 | | |
| | | | 3.9 | 78 ± 6 | | | |

TABLE 5-continued

Properties of drug-loaded hydrophilic matrices.

| Drug | Matrix composition | Drug content in the matrix (%) | Delivery rate in vitro $\mu g/cm^2h$ across: Carbosil | Human skin | $P_m$ ($10^4$) cm/h | $P_s$ ($10^4$) cm/h |
|---|---|---|---|---|---|---|
| 71. Propranolol | PVP-PEG | 13.8 | 118 ± 25 | 26.0 ± 15.0 | 10.6 ± 1.1 | 2.1 ± 0.2 |
| | | 7.4 | 79 ± 6 | | | |
| 72. Propranolol | PVCap-PEG | 13.8 | 145 ± 30 | | 13.0 ± 1.9 | |
| 73. Silabolin | PVP-PEG | 13.9 | 131 ± 30 | | 10.3 ± 0.5 | |
| | | 10.8 | 107 ± 21 | | | |
| | | 7.2 | 65 ± 14 | | | |
| 74. Foridone | PVP-PEG | 13.8 | 37.3 ± 4.5 | | 4.2 ± 1.5 | |
| | | 10.8 | 34.1 ± 4.0 | | | |
| | | 7.4 | 24.8 ± 3.0 | | | |
| | | 3.1 | 20.6 ± 1.9 | | | |
| 75. Clonidine | PVP-PEG | 7.7 | 26.8 ± 0.8 | 0.75 ± 0.04 | 4.0 ± 1.1 | 0.6 ± 0.2 |
| | | 1.4 | 5 ± 2 | 0.78 ± 0.1 | | |
| 76. Cytisine | PVP-PEG | 7.4 | 21 ± 3 | 9.0 ± 4.0 | 3.0 ± 0.5 | 1.3 ± 0.5 |
| 77. Phenazepam | PVP-PEG | 7.4 | 11 ± 2 | | 1.4 ± 0.3 | |
| | | 6.8 | 7 ± 2 | | | |
| 78. Nifedipin | PVP-PEG | 15.4 | 19 ± 3 | | 1.3 ± 0.2 | |
| 79. Fluacizin | PVP-PEG | 13.8 | 5 ± 1 | 6 ± 2 | 0.4 ± 0.1 | 0.4 ± 0.1 |
| 80. Salbutamol | PVP-PEG | 13.8 | 0.10 ± 0.04 | | 0.003 | |
| 81. Salbutamol | PVCap-PEG | 13.8 | 4.9 ± 1 | | 0.4 ± 0.1 | |
| 82. Chinosol | PVP-PEG | 3.0 | n/a | n/a | n/a | n/a |

As follows from the data in Table 5, the hydrophilic PSA matrices based on both the PVP and PVCap blends with PEG-400 (36 wt. % of the plasticizer in the blends) provide high delivery rates through both the skin-imitating Carbosil membrane and human skin epidermis. As comparative data in the Table 6 indicate, the hydrophilic PSA matrices allow us to enhance appreciably the rates of drug delivery compared to known hydrophobic PSAs such as PIB, PDMS and styrene-butadiene rubbers. In turn, the rates of drug delivery from the PVCap-PEG matrices are enhanced compared to the PVP-PEG matrix (compare examples 66 and 67, 71 and 72, 80 and 81).

TABLE 6

Comparative study of in vitro drug delivery rates ($\mu g/cm^2h$) from the hydrophilic PVP-PEG matrix and conventional hydrophobic matrices

| Drug | Delivery rate from hydrophilic matrix via Carbosil | Release rate from hydrophobic matrices | Composition of hydrophobic matrix |
|---|---|---|---|
| Aminostigmine | 625 ± 20 | 8 ± 1 | Styrene butadiene rubber |
| Nitroglycerin | 160 ± 40 | 80 ± 10 | PDMS, (Nitroderm ® TTS) |
| Silabolin | 131 ± 30 | 16 ± 7 | Styrene butadiene rubber |
| Propranolol | 118 ± 25 | 56 ± 4 | Styrene butadiene rubber |
| Clonidine | 5 ± 2 | 1.6 ± 0.2 | PIB (Catapress ® TTS) |

Drug targeting is necessary not only in systemic transdermal delivery, but also in topical delivery. Thus, the stratum corneum and epidermis are the targets for antifungal drugs and germicides. Ointments have often proven inconvenient to use and require multiple repeated daily application. Patches have now been developed that are more convenient to use and administered twice weekly, thereby improving patient acceptability. The application of a topical dermal patch (TDP) to human skin allows localization of drug concentration in damaged skin and does not involve the entire body. Furthermore, the continuous drug contact with the damaged tissue permits one to accelerate the recovery of diseased or wounded skin. For this purpose, a patch should be a non-occlusive. Hydrophilic PSA matrix, covered by a moisture permeable textile material as a backing, meets best this requirement.

Example 82 refers to an antifungal topical dermal patch based on the PVP-PEG PSA matrix. The patch is composed of a nonocclusive cotton textile backing on one side of the drug-loaded PVP-PEG adhesive matrix and a protective layer on the other side, which is removed before patch application to the skin. The patch is designed for topical targeted treatment of mycosis and contains 3% of chinosol (8-hydroxyquinoline sulfate) as an antifungal agent. The salt form of the drug serves to reduce its percutaneous absorption into systemic circulation. As the result, in vivo chinosol release rate from the Chinosive TDP in human volunteers averages only 0.42 $\mu g/cm^2$ h as has been evaluated from the drug remainder in the patch removed from the skin. As clinical studies with volunteers have shown, the topical antifungal monotherapy with the chinosol-containing patch results in essential acceleration of the treatment compared to the control group treated by the clotrimazol.

Thus, the hydrophilic PSA matrices outlined by this invention provide the performance properties useful in application dosage forms designed for transdermal and dermal drug delivery.

What is claimed is:

[1. A method of preparing an adhesive composition having an optimized degree of adhesion, comprising:

(a) preparing a plurality of compositions each comprised of a hydrophilic polymer having a glass transition temperature $T_{g\,pol}$ admixed with a plasticizer miscible therewith and having a glass transition temperature $T_{g\,pl}$ and capable of covalently or noncovalently crosslinking the hydrophilic polymer, wherein the weight fraction of the hydrophilic polymer in each composition is $w_{pol}$, and the weight fraction of the plasticizer in each composition is $w_{pl}$;

(b) calculating predicted glass temperatures $T_{g\ predicted}$ for each composition using the Fox equation (1)

$$\frac{1}{T_{g\ predicted}} = \frac{w_{pol}}{T_{g_{pol}}} + \frac{w_{pl}}{T_{g_{pl}}} \quad (1)$$

and plotting $T_{g\ predicted}$ versus $w_{pl}$ for each composition;

(c) determining the glass transition temperature $T_{g\ actual}$ for each composition, and plotting $T_{g\ actual}$ versus $w_{pl}$ for each composition;

(d) identifying the region of the plots of (b) and (c) wherein $T_{g\ actual}$ is less than $T_{g\ predicted}$; such that there is a negative deviation from $T_{g\ predicted}$;

(e) within the region identified in (d), identifying the optimum weight fraction of plasticizer $w_{pl\ optimum}$ at which the negative deviation from $T_{g\ predicted}$ is at a maximum; and (f) admixing a monomeric precursor to the hydrophilic polymer and the plasticizer under polymerizing conditions to provide an adhesive composition having an optimized degree of adhesion, wherein the weight fraction of plasticizer in the composition is $w_{pl\ optimum}$, and the weight fraction of the hydrophilic polymer in the composition is $1-w_{pl\ optimum}$.]

[2. The method of claim 1, wherein the plasticizer is capable of covalently crosslinking the hydrophilic polymer.]

[3. The method of claim 1, wherein the plasticizer is capable of noncovalently crosslinking the hydrophilic polymer.]

[4. The method of claim 1, wherein the plasticizer is capable of crosslinking the hydrophilic polymer by hydrogen bonding thereto.]

[5. A method of preparing an adhesive composition having an optimized degree of adhesion, comprising:

(a) preparing a plurality of compositions each comprised of a hydrophilic polymer having a glass transition temperature $T_{g\ pol}$ admixed with a plasticizer miscible therewith and having a glass transition temperature $T_{g\ pl}$ and capable of covalently or noncovalently crosslinking the hydrophilic polymer, wherein the weight fraction of the hydrophilic polymer in each composition is $w_{pol}$, and the weight fraction of the plasticizer in each composition is $w_{pl}$, such that $w_{pol}$ is equal to $1-w_{pl}$;

(b) calculating predicted glass temperatures $T_{g\ predicted}$ for each composition using the Fox equation (1)

$$\frac{1}{T_{g\ predicted}} = \frac{w_{pol}}{T_{g_{pol}}} + \frac{w_{pl}}{T_{g_{pl}}} \quad (1)$$

and plotting $T_{g\ predicted}$ versus $w_{pl}$ for each composition;

(c) determining the glass transition temperature $T_{g\ actual}$ for each composition, and plotting $T_{g\ actual}$ versus $w_{pl}$ for each composition;

(d) identifying the region of the plots of (b) and (c) wherein $T_{g\ actual}$ has a predetermined deviation from $T_{g\ predicted}$; and (e) admixing a monomeric precursor to the hydrophilic polymer and the plasticizer under polymerizing conditions to provide an adhesive composition having a desired degree of adhesion, wherein the weight percent of plasticizer in the composition corresponds to a value within the region identified in section (d).]

[6. The method of claim 5, wherein the plasticizer is capable of covalently crosslinking the hydrophilic polymer.]

[7. The method of claim 5, wherein the plasticizer is capable of noncovalently crosslinking the hydrophilic polymer.]

[8. The method of claim 5, wherein the plasticizer is capable of crosslinking the hydrophilic polymer by hydrogen bonding thereto.]

[9. The method of claim 1, wherein the difference between $T_{g\ pol}$ and $T_{g\ pl}$ is at least about 50° C., such that $T_{g\ actual}$ for each composition is determined solely by $T_{g\ pl}$.]

[10. The method of claim 2, wherein the difference between $T_{g\ pol}$ and $T_{g\ pl}$ is at least about 50° C., such that $T_{g\ actual}$ for each composition is determined solely by $T_{g\ pl}$.]

[11. The method of claim 1, wherein the hydrophilic polymer is selected from the group consisting of poly(N-vinyl lactams), poly(N-vinyl amides), poly(N-alkylacrylamides), polyacrylic acid, polymethacrylic acid, polyvinyl alcohol, polyvinylamine, and copolymers and blends thereof.]

[12. The method of claim 11, wherein the hydrophilic polymer is selected from the group consisting of poly(N-vinyl lactams), poly(N-vinyl amides), poly(N-alkylacrylamides), and copolymers and blends thereof.]

[13. The method of claim 12, wherein the hydrophilic polymer is a poly(N-vinyl lactam).]

[14. The method of claim 13, wherein the hydrophilic polymer is a poly(N-vinyl lactam) homopolymer.]

[15. The method of claim 14, wherein the poly(N-vinyl lactam) is selected from the group consisting of polyvinyl pyrrolidone, polyvinyl caprolactam, and blends thereof.]

[16. The method of claim 15, wherein the poly(N-vinyl lactam) is polyvinyl pyrrolidone.]

[17. The method of claim 15, wherein the poly(N-vinyl lactam) is polyvinyl caprolactam.]

[18. The method of claim 12, wherein the hydrophilic polymer is a poly(N-vinyl amide).]

[19. The method of claim 18, wherein the poly(N-vinyl amide) is polyacetamide.]

[20. The method of claim 12, wherein the hydrophilic polymer is a poly(N-alkylacrylamide).]

[21. The method of claim 20, wherein the poly(N-alkylacrylamide) is polymethacrylamide or poly(N-isopropyl acrylamide).]

[22. The method of claim 1, wherein the hydrophilic polymer has a weight average molecular weight in the range of approximately 100,000 to 2,000,000.]

[23. The method of claim 22, wherein the hydrophilic polymer has a weight average molecular weight in the range of approximately 500,000 to 1,500,000.]

[24. The method of claim 1, wherein $T_{g\ pl}$ is in the range of approximately −100° to −30° C.]

[25. The method of claim 24, wherein the melting temperature of the plasticizer is lower than about 50° C.]

[26. The method of claim 1, wherein the plasticizing agent has a molecular weight in the range of about 45 to 800.]

[27. The method of claim 26, wherein the plasticizing agent has a molecular weight in the range of about 45 to 600.]

[28. The method of claim 24, wherein the plasticizing agent has a molecular weight in the range of about 300 to 600.]

[29. The method of claim 26, wherein the plasticizing agent is selected from the group consisting of of polyalcohols, monomeric and oligomeric alkylene glycols, polyalkylene glycols, carboxyl-teminated polyalkylene glycols, amino-terminated polyalkylene glycols, ether alcohols, alkane diols and carbonic diacids.]

[30. The method of claim 29, wherein the plasticizing agent is selected from the group consisting of polyalkylene glycols and carboxyl-terminated polyalkylene glycols.]

[31. The method of claim 30, wherein the plasticizing agent is selected from the group consisting of polyethylene glycol and carboxyl-terminated polyethylene glycol.]

[32. The method of claim 31, wherein the plasticizing agent is polyethylene glycol.]

[33. The method of claim 1, wherein the adhesive composition further includes a photoinitator, and, following step (e), the adhesive composition is crosslinked using radiation.]

[34. The method of claim 1, wherein step (e) further includes admixing the hydrophilic polymer and the plasticizing agent with at least one chemical crosslinking agent that covalently crosslinks the adhesive composition.]

[35. The method of claim 34, wherein the at least one chemical crosslinking agent is selected from the group consisting of dipentaerythritol pentaacrylate, ethylene glycol dimethacrylate, and triethylene glycol dimethacrylate.]

[36. The method of claim 35, wherein the weight ratio of the chemical crosslinking agent to the hydrophilic polymer is below 5%.]

[37. The method of claim 1, wherein, following step (e), the adhesive composition is crosslinked using heat.]

[38. The method of any one of claim 33, 34 or 36, wherein the crosslinking density of the crosslinked adhesive composition provides a swell ratio in the range of approximately 20 to approximately 60.]

39. [A] *An extruded composition comprising a* hydrophilic pressure sensitive adhesive composition comprising (1) a hydrophilic polymer *selected from non-crosslinked poly(N-vinyl lactam)s and copolymers and blends thereof* having a glass transition temperature, $T_{g\,pol}$, and (2) a complementary hydroxyl-terminated or carboxyl-terminated short-chain plasticizing agent *selected from the group consisting of monomeric and oligomeric alkylene glycols, polyalkylene glycols, and carboxyl-terminated polyalkylene glycols* having a glass transition temperature, $T_{g\,pl}$, and capable of hydrogen bonding or electrostatic bonding to the hydrophilic polymer, wherein the weight ratio of hydrophilic polymer to complementary short-chain plasticizing agent [is selected so to provide] *provides* a [predetermined] deviation in (a) the actual glass transition temperature, $T_{g\,actual}$, of the composition from (b) the predicted glass transition temperature, $T_{g\,predicted}$, calculated for the composition using *the* Fox equation (1)

$$\frac{1}{T_{g\,predicted}} = \frac{w_{pol}}{T_{g_{pol}}} + \frac{w_{pl}}{T_{g_{pl}}}, \quad (1)$$

*$w_{pol}$ is the weight fraction of the hydrophilic polymer in the composition, $w_{pl}$ is the weight fraction of the plasticizer in the composition, and the ratio of the weight average molecular weight of the hydrophilic polymer to the complementary short-chain plasticizing agent is within a range of about 1,250 and 20,000.*

40. The *extruded* composition of claim 39, wherein the [predetermined] deviation is the maximum negative deviation.

41. [A hydrophilic, substantially nonaqueous pressure sensitive adhesive composition comprising (a) a hydrophilic polymer, and (b) a complementary hydroxyl-terminated or carboxyl-terminated short-chain plasticizing agent capable of hydrogen bonding or electrostatic bonding to the hydrophilic polymer, wherein the ratio of hydrogen bonding to covalent crosslinks is selected to optimize adhesive strength, cohesive strength, and hydrophilicity;

wherein the plasticizing agent decreases the glass transition temperature $T_g$ of the hydrophilic composition according to Fox equation (1)

$$\frac{1}{T_{g\,predicted}} = \frac{w_{pol}}{T_{g_{pol}}} + \frac{w_{pl}}{T_{g_{pl}}} \quad (1)$$

wherein $T_{g\,predicted}$ is the predicted glass transition temperature of the hydrophilic polymer/plasticizer composition, $w_{pol}$ is the weight fraction of the hydrophilic polymer in the composition, $w_{pl}$ is the weight fraction of the plasticizer in the composition, $T_{g\,pol}$ is the glass transition temperature of the hydrophilic polymer, and $T_{g\,pl}$ is the glass transition temperature of the plasticizer; and] *The extruded composition of claim 40,* wherein maximum adhesiveness is achieved at a point of maximum negative deviation from $T_{g\,predicted}$.

42. [A] *The extruded* hydrophilic pressure sensitive adhesive composition [comprising (a) a hydrophilic polymer and (b) a complementary hydroxyl-terminated or carboxyl-terminated short-chain plasticizing agent capable of hydrogen bonding or electrostatic bonding to the hydrophilic polymer] *according to claim 39*, wherein the hydrophilic polymer and the plasticizing agent are *noncovalently* crosslinked to [a predetermined] *an* extent *effective*, [and the extent of crosslinking and] *along with* the ratio of the hydrophilic polymer to the plasticizing agent [are selected], to optimize the hydrophilicity, adhesive strength and cohesive strength of the composition[;

wherein the plasticizing agent decreases the glass transition temperature $T_g$ of the hydrophilic composition according to Fox equation (1)

$$\frac{1}{T_{g\,predicted}} = \frac{w_{pol}}{T_{g_{pol}}} + \frac{w_{pl}}{T_{g_{pl}}} \quad (1)$$

wherein $T_{g\,predicted}$ is the predicted glass transition temperature of the hydrophilic polymer/plasticizer composition, $w_{pol}$ is the weight fraction of the hydrophilic polymer in the composition, $w_{pl}$ is the weight fraction of the plasticizer in the composition, $T_{g\,pol}$ is the glass transition temperature of the hydrophilic polymer, and $T_{g\,pl}$ is the glass transition temperature of the plasticizer; and wherein maximum adhesiveness is achieved at a point of maximum negative deviation from $T_{g\,predicted}$].

43. The *extruded* composition of any one of claims 39, 41 or 42, wherein the adhesive composition is substantially nonaqueous.

44. The *extruded* composition of claim 39, wherein the difference between $T_{g\,pol}$ and $T_{g\,pl}$ is at least about 50° C., such that $T_{g\,actual}$ for each composition is determined solely by $T_{g\,pl}$.

[45. The composition of claim 39, wherein the hydrophilic polymer is selected from the group consisting of poly(N-vinyl lactams), poly(N-vinyl amides), poly(N-alkylacrylamides), polyacrylic acid, polymethacrylic acid, polyvinyl alcohol, polyvinylamine, and copolymers and blends thereof.]

[46. The composition of claim 45, wherein the hydrophilic polymer is selected from the group consisting of poly(N-vinyl lactams), poly(N-vinyl amides), poly(N-alkylacrylamides), and copolymers and blends thereof.]

47. The *extruded* composition of claim [46] *39*, wherein the hydrophilic polymer is a poly(N-vinyl lactam).

48. The *extruded* composition of claim 47, wherein the hydrophilic polymer is a poly(N-vinyl lactam) homopolymer.

49. The *extruded* composition of claim 48, wherein the poly(N-vinyl lactam) is selected from the group consisting of polyvinyl pyrrolidone, polyvinyl caprolactam, and blends thereof.

50. The *extruded* composition of claim 49, wherein the poly(N-vinyl lactam) is polyvinyl pyrrolidone.

51. The composition of claim 49, wherein the poly(N-vinyl lactam) is polyvinyl caprolactone.

[52. The composition of claim 39, wherein the hydrophilic polymer is a poly(N-vinyl amide).]

[53. The composition of claim 52, wherein the poly(N-vinyl amide) is polyacetamide.]

[54. The composition of claim 39, wherein the hydrophilic polymer is a poly(N-alkylacrylamide).]

[55. The composition of claim 54, wherein the poly(N-alkylacrylamide) is polymethacrylamide or poly(N-isopropyl acrylamide).]

[56. The composition of claim 39, wherein the hydrophilic polymer has a weight average molecular weight in the range of approximately 100,000 to 2,000,000.]

57. The *extruded* composition of claim [56] *39*, wherein the hydrophilic polymer has a weight average molecular weight in the range of approximately 500,000 to 1,500,000.

58. The *extruded* composition of claim 39, wherein $T_{g\ pl}$ is in the range of approximately −100° to −30° C.

59. The *extruded* composition of claim 58, wherein the melting temperature of the plasticizer is lower than about 50° C.

60. The *extruded* composition of claim 39, wherein the plasticizing agent has a molecular weight in the range of about 45 to 800.

61. The *extruded* composition of claim 60, wherein the plasticizing agent has a molecular weight in the range of about 45 to 600.

62. The *extruded* composition of claim 61, wherein the plasticizing agent has a molecular weight in the range of about 300 to 600.

[63. The composition of claim 60, wherein the plasticizing agent is selected from the group consisting of of polyalcohols, monomeric and oligomeric alkylene glycols, polyalkylene glycols, carboxyl-teminated polyalkylene glycols, amino-terminated polyalkylene glycols, ether alcohols, alkane diols and carbonic diacids.]

64. The *extruded* composition of claim [63] *60*, wherein the plasticizing agent is selected from the group consisting of polyalkylene glycols and carboxyl-terminated polyalkylene glycols.

65. The *extruded* composition of claim 64, wherein the plasticizing agent is selected from the group consisting of polyethylene glycol and carboxyl-terminated polyethylene glycol.

66. The *extruded* composition of claim 65, wherein the plasticizing agent is polyethylene glycol.

[67. The composition of claim 39, wherein the composition is covalently crosslinked.]

[68. The composition of claim 67, wherein the crosslinking density of the crosslinked adhesive composition provides a swell ratio in the range of approximately 20 to approximately 60.]

69. A therapeutic system for the topical or transdermal administration of a pharmacologically active agent, comprising:

(A) a drug reservoir comprising (1) a substantially non-aqueous pressure sensitive adhesive matrix [of] *comprising* a hydrophilic polymer *selected from non-crosslinked poly(N-vinyl lactam)s and copolymers and blends thereof* having a glass transition temperature, $T_{g\ pol}$, and a complementary hydroxyl-terminated or carboxyl-terminated short-chain plasticizing agent *selected from the group consisting of monomeric and oligomeric alkylene glycols, polyalkylene glycols, and carboxyl-terminated polyalkylene glycols* having a glass transition temperature $T_{g\ pl}$ and capable of hydrogen bonding or electrostatic bonding to the hydrophilic polymer, wherein the weight ratio of hydrophilic polymer to complementary short-chain plasticizing agent [is selected so to provide] *provides* a [predetermined] deviation in (a) the actual glass transition temperature, $T_{g\ actual}$, of the composition from (b) the predicted glass transition temperature $T_{g\ predicted}$ for the composition calculated using Fox equation (1)

$$\frac{1}{T_{g\ predicted}} = \frac{w_{pol}}{T_{g_{pol}}} + \frac{w_{pl}}{T_{g_{pl}}} \tag{1}$$

*and the ratio of the weight average molecular weight of the hydrophilic polymer to the complementary short-chain plasticizing agent is within a range of about 1,250 to 20,000,* and (2) a therapeutically effective amount of the active agent; and (B) a backing layer laminated to the drug reservoir that serves as the outer surface of the [device] *system* during use,

*wherein the drug reservoir comprising the pressure sensitive adhesive matrix and the active agent is in extruded form.*

70. The system of claim 69, wherein the [predetermined] deviation is the maximum negative deviation.

71. The system of claim 69, wherein the hydrophilic polymer is comprised of repeating units resulting from polymerization of an N-vinyl lactam monomer[, a carboxy vinyl monomer, a vinyl ester monomer, an ester of a carboxy vinyl monomer, a vinyl amide monomer, a hydroxy vinyl monomer, or a combination thereof].

[72. The system of claim 71, wherein the hydrophilic polymer is selected from the group consisting of poly(N-vinyl lactams), poly(N-vinyl amides), poly(N-alkylacrylamides), polyacrylic acid, polymethacrylic acid, polyvinyl alcohol, polyvinylamine, and copolymers and blends thereof.]

[73. The system of claim 72, wherein the hydrophilic polymer is selected from the group consisting of poly(N-vinyl lactams), poly(N-vinyl amides), poly(N-alkylacrylamides), and copolymers and blends thereof.]

74. The system of claim [73] *69*, wherein the hydrophilic polymer is a poly(N-vinyl lactam).

75. The system of claim 74, wherein the hydrophilic polymer is a poly(N-vinyl lactam) homopolymer.

76. The system of claim 75, wherein the poly(N-vinyl lactam) is selected from the group consisting of polyvinyl pyrrolidone, polyvinyl caprolactam, and blends thereof.

77. The system of claim 76, wherein the poly(N-vinyl lactam) is polyvinyl pyrrolidone.

78. The system of claim 76, wherein the poly(N-vinyl lactam) is polyvinyl caprolactone.

[79. The system of claim 73, wherein the hydrophilic polymer is a poly(N-vinyl amide).]

[80. The system of claim 79, wherein the poly(N-vinyl amide) is polyacetamide.]

[81. The system of claim 73, wherein the hydrophilic polymer is a poly(N-alkylacrylamide).]

[82. The system of claim 81, wherein the poly(N-alkylacrylamide) is polymethacrylamide or poly(N-isopropyl acrylamide).]

[83. The system of claim 69, wherein the hydrophilic polymer has a weight average molecular weight in the range of approximately 100,000 to 2,000,000. ]

84. The system of claim [83] *69*, wherein the hydrophilic polymer has a weight average molecular weight in the range of approximately 500,000 to 1,500,000.

85. The system of claim 69, wherein $T_{g\,pl}$ is at least 50° C. below $T_{g\,pol}$.

86. The system of claim 85, wherein $T_{g\,pl}$ is in the range of approximately −100° to −30° C.

87. The system of claim 69, wherein the melting temperature of the plasticizer is lower than about 50° C.

88. The system of claim 87, wherein the plasticizing agent has a molecular weight in the range of about 45 to 800.

89. The system of claim 88, wherein the plasticizing agent has a molecular weight in the range of about 45 to 600.

90. The system of claim 89, wherein the plasticizing agent has a molecular weight in the range of about 300 to 600.

[91. The system of claim 88, wherein the plasticizing agent is selected from the group consisting of of polyalcohols, monomeric and oligomeric alkylene glycols, polyalkylene glycols, carboxyl-teminated polyalkylene glycols, amino-terminated polyalkylene glycols, ether alcohols, alkane diols and carbonic diacids.]

92. The system of claim [91] *69*, wherein the plasticizing agent is selected from the group consisting of polyalkylene glycols and carboxyl-terminated polyalkylene glycols.

93. The system of claim 92, wherein the plasticizing agent is selected from the group consisting of polyethylene glycol and carboxyl-terminated polyethylene glycol.

94. The system of claim 93, wherein the plasticizing agent is polyethylene glycol.

[95. The system of claim 69, wherein the composition is covalently crosslinked.]

[96. The system of claim 95, wherein the crosslinking density of the crosslinked adhesive composition provides a swell ratio in the range of approximately 20 to approximately 60.]

97. The system of claim 69, wherein the backing layer is non-occlusive.

98. The system of claim 69, wherein the backing layer is occlusive.

*99. An extruded hydrophilic adhesive composition, comprising:*

*(a) a non-crosslinked hydrophilic polymer selected from polyvinylcaprolactone, polyvinylpyrrolidone, copolymers thereof, and blends of any of the foregoing;*

*(b) a plasticizing agent selected from the group consisting of monomeric and oligomeric alkylene glycols, polyalkylene glycols, and carboxyl-terminated polyalkylene glycols capable of hydrogen bonding to the hydrophilic polymer, having a glass transition temperature $T_g$ in the range of about −100° C. to about −30° C., and a melting temperature $T_m$ lower than about 20° C., wherein the weight ratio of the hydrophilic polymer to the plasticizing agent is in the range of approximately 1:1 to 4:1 and the ratio of the weight average molecular weight of the hydrophilic polymer to the complementary short-chain plasticizing agent is within a range of about 1,250 and 20,000, and*

*(c) an active agent,*

*wherein the composition is substantially nonaqueous, absorbs water upon application to a hydrated surface, and adheres thereto.*

*100. The extruded composition of claim 99, wherein the hydrophilic polymer is a blend of polymers selected from polyvinylcaprolactone, polyvinylpyrrolidone, and copolymers thereof.*

*101. The extruded composition of claim 99, wherein the plasticizing agent is selected from the group consisting of oligomeric alkylene glycols, polyalkylene glycols, and carboxyl-terminated alkylene glycols.*

*102. The extruded composition of claim 101, wherein the plasticizing agent is polyethylene glycol.*

*103. The extruded composition of claim 101, wherein the plasticizing agent is a carboxyl-terminated polyethylene glycol.*

*104. The extruded composition of claim 99, wherein the plasticizing agent has a molecular weight in the range of about 200 to 800.*

*105. The extruded composition of claim 104, wherein the plasticizing agent has a molecular weight in the range of about 300 to 600.*

*106. The extruded composition of claim 99, wherein the active agent is an anti-infective agent.*

*107. The extruded composition of claim 99, wherein the active agent is an anesthetic agent.*

*108. The extruded composition of claim 99, further including a non-woven material.*

*109. The extruded composition of claim 99, further including a woven material.*

*110. A system comprising (a) a monolithic matrix composed of the composition of claim 99, and (b) a backing layer.*

*111. The system of claim 110, wherein the backing layer is non-occlusive.*

*112. The system of claim 111, wherein the backing layer is occlusive.*

*113. The system of claim 110, wherein the backing layer is comprised of a flexible material.*

*114. The system of claim 110, wherein the backing layer is comprised of a material selected from the group consisting of polyesters, polyethylenes, polypropylene, polyurethane, and polyether amides.*

*115. The system of claim 106, wherein the backing layer is about 50 microns to about 250 microns in thickness.*

*116. A system comprising (a) a monolithic matrix comprised of the composition of claim 99, and (b) a rate-controlling membrane.*

*117. The system of claim 116, wherein the membrane is comprised of a polyolefinic material.*

*118. The system of claim 116, wherein the membrane is comprised of a material selected from the group consisting of polyethylene, polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, and ethylene-propylene copolymer.*

*119. The system of claim 110, further including a fabric layer.*

*120. The extruded composition of claim 39 or 99, or the therapeutic system of claim 69, wherein the hydrophilic polymer and the plasticizing agent are miscible.*

*121. The composition of claim 39 or 99, or the therapeutic system of claim 69, wherein the hydrophilic polymer and the plasticizing agent, when mixed, form a homogeneous blend that exhibits a single Tg intermediate between those of the unblended components.*

*122. The extruded composition of claim 39 or 99, or the therapeutic system of claim 69, wherein the hydrophilic polymer is polyvinyl pyrrolidone, the plasticizing agent is a polyethylene glycol having a molecular weight in a range from about 300 to 600, and the weight ratio of the hydrophilic polymer to the plasticizing agent is in a range from about 2.3 to 1.2.*

* * * * *